(12) United States Patent  
Belley et al.

(10) Patent No.: US 8,013,159 B2
(45) Date of Patent: Sep. 6, 2011

(54) QUINOLINE DERIVATIVES AS EP4 ANTAGONISTS

(75) Inventors: Michel Belley, Pierre Fonds (CA); Jason Burch, Westmount (CA); John Colucci, Kirkland (CA); Julie Farand, Montreal (CA); Mario Girard, Saint-Lazare (CA); Yongxin Han, Kirkland (CA)

(73) Assignee: Merck Canada Inc., Quebec (CA)

( * ) Notice: Subject to any disclaimer, the term of this patent is extended or adjusted under 35 U.S.C. 154(b) by 868 days.

(21) Appl. No.: 11/920,275

(22) PCT Filed: May 15, 2006

(86) PCT No.: PCT/CA2006/000789
§ 371 (c)(1), (2), (4) Date: Nov. 13, 2007

(87) PCT Pub. No.: WO2006/122403
PCT Pub. Date: Nov. 23, 2006

(65) Prior Publication Data
US 2009/0099226 A1    Apr. 16, 2009

Related U.S. Application Data

(60) Provisional application No. 60/682,589, filed on May 19, 2005.

(51) Int. Cl.
*C07D 471/00* (2006.01)
(52) U.S. Cl. ........................................................ 546/84
(58) Field of Classification Search .................. 546/84
See application file for complete search history.

(56) References Cited

U.S. PATENT DOCUMENTS
2004/0157804 A1* 8/2004 Chen et al. ................ 514/151

FOREIGN PATENT DOCUMENTS

| CA | 2 466 757 | 6/2003 |
| CA | 2 469 048 | 6/2003 |
| CA | 2 502 914 | 5/2004 |
| EP | 1 236 468 A1 | 9/2002 |
| EP | 752 421 | 12/2005 |
| EP | 1 736 467 A1 | 12/2006 |
| WO | WO 96/06822 | 3/1996 |
| WO | WO 96/11902 | 4/1996 |
| WO | WO 00/21542 | 4/2000 |
| WO | WO 02/50032 A1 | 6/2002 |
| WO | WO 02/50033 A1 | 6/2002 |
| WO | WO 0250032 * | 6/2002 |
| WO | WO 2004/019932 A1 | 3/2004 |
| WO | WO 2004/035576 A2 | 4/2004 |
| WO | WO 2004/035577 A2 | 4/2004 |
| WO | WO 2004/096807 A2 | 11/2004 |
| WO | WO 2005/117904 A2 | 12/2005 |
| WO | WO 2006/024628 A1 | 3/2006 |

OTHER PUBLICATIONS

Burch et al. Bioorganic & Medicinal Chemistry Letters (2008), 18(6), 2048-2054.*

* cited by examiner

*Primary Examiner* — Nizal Chandrakumar
(74) *Attorney, Agent, or Firm* — Maria V. Marucci; Valerie J. Camara

(57) ABSTRACT

The invention is directed to quinoline derivatives as prostaglandin E type receptor antagonists useful for the treatment of EP4 mediated diseases or conditions, such as acute and chronic pain, osteoarthritis, rheumatoid arthritis and cancer. The derivatives have the following structure of formula (I): wherein A and B represents either a nitrogen atom or a CH group with the proviso that they cannot both simultaneously be CH, Q can represent a nitrogen or a carbon atom, and Y and Z are either a nitrogen atom, a N(O) group or a $C(R^5)$ group. Pharmaceutical compositions comprising the derivatives of formula (I) are also included.

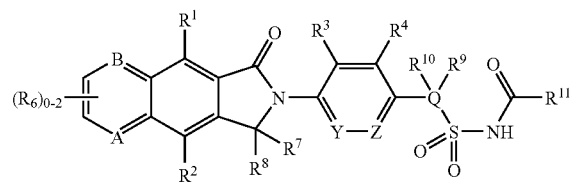

(I)

17 Claims, No Drawings

QUINOLINE DERIVATIVES AS EP4 ANTAGONISTS

CROSS REFERENCE TO RELATED APPLICATIONS this is a National filing under 35 USC 371 of PCT/CA2006/000789, filed May 15, 2006, which claims priority from U.S. Ser. No. 60/682,589,filed May 19, 2005.

BACKGROUND OF THE INVENTION

This invention relates to compounds and methods for treating prostaglandin E mediated diseases, and certain pharmaceutical compositions thereof. More particularly, the compounds of the invention are structurally different from NSAIDs and opiates, and are antagonists of the pain and inflammatory effects of E-type prostaglandins.

Three review articles describe the characterization and therapeutic relevance of the prostanoid receptors as well as the most commonly used selective agonists and antagonists: *Eicosanoids. From Biotechnology to Therapeutic Applications*, Folco, Samuelsson, Maclouf, and Velo eds, Plenum Press, New York, 1996, chap. 14, 137-154; Journal of Lipid Mediators and Cell Signalling, 1996, 14, 83-87; and Prostaglandins and Other Lipid Mediators, 2002, 69, 557-573.

Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, have effects on vascular homeostasis, reproduction, gastrointestinal functions and bone metabolism. These compounds may have a diminished ability to induce some of the mechanism-based side effects of NSAIDs which are indiscriminate cyclooxygenase inhibitors. In particular, the compounds are believed to have a reduced potential for gastrointestinal toxicity, a reduced potential for renal side effects, a reduced effect on bleeding times and a lessened ability to induce asthma attacks in aspirin-sensitive asthmatic subjects.

In The Journal of Clinical Investigation (2002, 110, 651-658), studies suggest that chronic inflammation induced by collagen antibody injection in mice is mediated primarily through the EP4 subtype of $PGE_2$ receptors. Patent application publications WO 96/06822 (Mar. 7, 1996), WO 96/11902 (Apr. 25, 1996) and EP 752421-A1 (Jan. 8, 1997) disclose compounds as being useful in the treatment of prostaglandin mediated diseases.

The present invention is directed to novel compounds that are antagonists of the EP4 subtype of $PGE_2$ receptors. The compounds would therefore be useful for the treatment of diseases or conditions mediated by the EP4 receptor, such as acute and chronic pain, osteoarthritis, rheumatoid arthritis and cancer

SUMMARY OF THE INVENTION

The invention is directed to quinoline derivatives as EP4 receptor antagonists useful for the treatment of EP4 mediated diseases or conditions, such as acute and chronic pain, osteoarthritis, rheumatoid arthritis and cancer. Pharmaceutical compositions and methods of use are also included.

DETAILED DESCRIPTION OF THE INVENTION

The invention encompasses a compound of Formula I

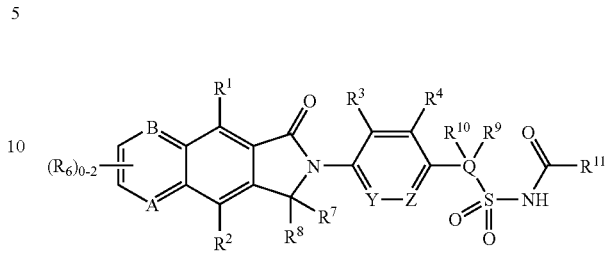

I or a pharmaceutically acceptable salt thereof, wherein:

A is selected from the group consisting of N or CH,

B is selected from the group consisting of N or CH, with the proviso that A and B cannot both simultaneously be CH;

Y and Z are independently selected from the group consisting of: N, N(O) and C($R^5$);

Q is N or C:

$R^1$ to $R^6$ are independently selected from the group consisting of: H, halogen, $C_{1-6}$alkyl $C_{3-6}$cycloalkyl, $C_{1-6}$perfluoroalkyl, $C_{1-6}$alkoxy, $C_{1-6}$perfluoroalkoxy, $C_{3-6}$cycloalkoxy, $C_{3-6}$cycloalkylmethoxy, $NH_2$, —$NHC_{1-4}$alkyl, —$N(C_{1-4}$alkyl$)_2$, $NO_2$, OH and CN;

$R^7$ and $R^8$ are independently selected from the group consisting of: H and $C_{1-6}$alkyl or $R^7$ and $R^8$ can join to make a carbonyl or 3-6 membered monocyclic cycloalkane ring;

$R^9$ and $R^{10}$ are selected from the group consisting of: H and $C_{1-6}$alkyl or $R^9$ and $R^{10}$ can join to make a 3-6 membered monocyclic cycloalkane ring, with the proviso that $R^9$ is not present when Q is N;

$R^{11}$ is selected from the group consisting of: (a) $C_{1-6}$alkyl, (b) $C_{3-6}$cycloalkyl, (c) $C_{3-6}$cycloalkyl substituted by one to three substituents independently selected from $R^{12}$; (d) aryl, (e) aryl substituted by one to three substituents independently selected from $R^{12}$, (f) heteroaryl, (g) heteroaryl substituted by one to three substituents independently selected from $R^{12}$, (h) heterocyclyl, (i) heterocyclyl substituted by one to three substituents independently selected from $R^{12}$, (j) —$C_{1-6}$alkylaryl, (k) —$C_{1-6}$alkylaryl substituted by one to three substituents independently selected from $R^{12}$, (k) —$C_{1-6}$alkyl-$C_{3-6}$cycloalkyl; (l) —$C_{1-6}$alkyl-$C_{3-6}$cycloalkyl substituted by one to three substituents independently selected from $R^{12}$; (m) —$C_{1-6}$alkylheteroaryl; (n) —$C_{1-6}$alkylheteroaryl substituted by one to three substituents independently selected from $R^{12}$; (o) —$C_{1-6}$alkylheterocyclyl; and (p) —$C_{1-6}$alkylheterocyclyl substituted by one to three substituents independently selected from $R^{12}$; and fused analogs of (b) to (p); and $R^{12}$ is selected from the group consisting of halogen $C_{1-6}$alkyl, $C_{1-6}$ perfluoroalkyl, $C_{3-6}$cycloalkyl, $C_{1-6}$alkoxy, $C_{1-6}$perfluoroalkoxy, $C_{3-6}$cycloalkoxy, NH2, —$NHC_{1-4}$alkyl or —$N(C_{1-4}$alkyl$)_2$, $NO_2$ and OH. The invention also encompasses compounds of Formula I wherein $R^3$ is other than H.

The invention also encompasses a genus of compounds of Formula Ia

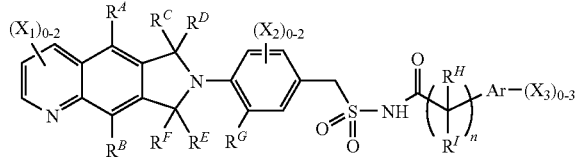

or a pharmaceutically acceptable salt thereof, wherein:
n is 0 or 1;
Ar is selected from the group consisting of $C_{3-6}$cycloalkyl, aryl, heteroaryl and heterocyclyl, or a fused analog of $C_{3-6}$cycloalkyl, aryl, heteroaryl and heterocyclyl;
$R^A$ and $R^B$ are independently selected from the group consisting of $C_{1-4}$alkyl, $C_{1-4}$perfluoroalkyl, $C_{1-4}$alkoxy, $C_{1-4}$ perfluoroalkoxy, $C_{3-6}$cycloalkyl, $C_{3-6}$cycloalkoxy and $C_{3-6}$cycloalkylmethoxy;
$R^C$ and $R^D$ or $R^E$ and $R^F$ or both are joined together to from carbonyl, and otherwise are hydrogen;
$R^G$ is selected from the group consisting of: F, Cl, Br, I, methyl, ethyl, methoxy, $CF_3$, $CF_3O$— and CN;
$R^H$ and $R^I$ are independently hydrogen or methyl; or $R^H$ and $R^I$ may be joined together to form a $C_{3-6}$cycloalkyl ring; and
each $X_1$, $X_2$ and $X_3$ is independently selected from the group consisting of: F, Cl, Br, I, methyl, ethyl, methoxy, $CF_3$, $CF_3O$— and OH.

Within this genus, the invention encompasses a compound of Formula Ia wherein $R^A$ and $R^B$ are ethoxy.

Also within this genus, the invention encompasses a sub-genus of compounds of Formula Ia wherein $R^C$ and $R^D$ are joined together to form carbonyl and $R^E$ and $R^F$ are hydrogen.

Also within this genus, the invention encompasses a sub-genus of compounds of Formula Ia wherein $R^E$ and $R^F$ are joined together to form carbonyl and $R^C$ and $R^D$ are hydrogen.

Also within this genius, the invention encompasses a sub-genus of compounds of Formula Ia wherein both $R^C$ and $R^D$ are joined together to form carbonyl and $R^E$ and $R^F$ are joined together to form carbonyl.

Also within this genus, the invention encompasses a sub-genus of compounds of Formula Ia wherein $R^G$ is F, Cl, Br, I or methyl.

Also within this genus, the invention encompasses a sub-genus of compounds of Formula Ia wherein n is 1 and Ar is selected from the group consisting of phenyl, naphthyl and pyridyl; or n is 0 and Ar is selected from the group consisting of: indanyl and tetrahydronaphthyl. Within this sub-genus, the invention encompasses a class of compounds of Formula Ia wherein n is 1 and Ar is phenyl. Within this class, the invention encompasses a sub-class of compounds wherein at least one $X_3$ is present and is attached at the 2-position on the phenyl ring. Within this sub-class, the invention encompasses compounds of Formula Ia wherein $X_3$ is methoxy.

Also within the genus, the invention encompasses a sub-genus of compounds of Formula Ia wherein: n is 1; Ar is phenyl; $R^A$ and $R^B$ are ethoxy; $R^G$ is methyl; and $X_1$ and $X_2$ are not present.

Within this sub-genus of compounds, the invention encompasses a class of compounds wherein $R^C$ and $R^D$ are joined together to form carbonyl and $R^E$ and $R^F$ are hydrogen.

Within this sub-genus of compounds, the invention encompasses a class of compounds wherein $R^E$ and $R^F$ are joined together to form carbonyl and $R^C$ and $R^D$ are hydrogen.

Within this sub-genus of compounds, the invention encompasses a class of compounds wherein both $R^C$ and $R^D$ are joined together to form carbonyl and $R^E$ and $R^F$ are joined together to form carbonyl.

Within this sub-genus of compounds the invention encompasses a class of compounds wherein at least one $X_3$ is present and is attached at the 2-position on the phenyl ring.

The invention also encompasses the examples that follow.

The invention also encompasses a pharmaceutical composition comprising a compound of Formula I in admixture with one or more physiologically acceptable carriers or excipients.

The invention also encompasses a compound of Formula I or a pharmaceutically acceptable derivative thereof for use in human or veterinary medicine.

The invention also encompasses a method of treating a human or animal subject suffering from a condition which is mediated by the action of PGE2 at EP4 receptors, which method comprises administering to said subject an effective amount of a compound of Formula I.

The invention also encompasses the use of a compound of Formula I for the manufacture of a therapeutic agent for the treatment of a condition which is mediated by the action of PGE2 at EP4 receptors.

Definitions

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Perfluoroalkyl" means alkyl as defined above wherein all the hydrogen atoms have been replaced by fluoro atoms.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having, from 3 to 10 carbon atoms. A "fused analog" of cycloalkyl means a monocyclic rings fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, and the like.

"Alkoxy" means alkoxy groups of a straight or branched having the indicated number of carbon atoms. $C_{1-6}$alkoxy, for example, includes methoxy, ethoxy, propoxy, isopropoxy, and the like.

"Cycloalkoxy" means cycloalkyl as defined above bonded to an oxygen atom, such as cyclopropyloxy.

"Perfluoroalkoxy" means alkoxy as defined above therein all the hydrogen atoms have been replaced by fluoro atoms.

"Aryl" means mono- or bicyclic aromatic rings containing only carbon atoms. A "fused analog" of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. A "fused analog" of heteroaryl means a heteroaryl group fused to a monocyclic cycloalkyl or monocyclic heterocyclyl group in which the point of attachment is on the aromatic portion. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. A "fused analog" of heterocyclyl means a monocyclic heterocycle fused to an aryl or heteroaryl group in which the point of attachment is on the non-aromatic portion. Examples of "heterocyclyl" and fused analogs thereof include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" includes fluorine, chlorine, bromine and iodine.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The compounds of the invention are antagonists of the EP4 receptor and are therefore useful in treating EP4 receptor mediated diseases.

In view of their ability to bind to the EP4 receptor, the compounds of the invention are useful in the treatment of the disorders that follow. Thus, the compounds of Formula I are useful as analgesics. For example they are useful in the treatment of chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of the invention are particularly useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that 25 precipitated them. Neuropathic pain syndromes include: diabetic neuropathy; sciatica; non-specific lower back pain; multiple sclerosis pain; fibromyalgia; HIV related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthes; a), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of Formula I are also useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome pigeon fancier's disease, farmer's lung, CORD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds of Formula I are also useful in the treatment of immunological diseases such as autoimmune diseases, immunological deficiency diseases or organ transplantation. The compounds of Formula I are also effective in increasing the latency of HIV infection.

The compounds of Formula I are also useful in the treatment of diseases of abnormal platelet function (e.g. occlusive vascular diseases).

The compounds of Formula I are also useful for the preparation of a drug with diuretic action.

The compounds of Formula I are also useful in the treatment of impotence or erectile dysfunction.

The compounds of Formula I and Ia are also useful in the treatment of bone disease characterized by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis. In a further aspect compounds of Formula I may be useful in inhibiting bone resorption and/or promoting bone generation.

The compounds of Formula I and Ia are also useful for attenuating the hemodynamic side effects of NSAIDs and COX-2 inhibitors.

The compounds of Formula I are also useful in the treatment of cardiovascular diseases such as hypertension or myocardial ischemia; functional or organic venous insufficiency; varicose therapy; haemorrhoids; and shock states associated with a marked drop in arterial pressure (e.g. septic shock).

The compounds of Formula I are also useful in the treatment of neurodegenerative diseases and neurodegeneration such as dementia, particularly degenerative dementia (including senile dementia, Alzheimer's disease, Pick's disease, Huntingdon's chores, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment. The compounds of Formula I are also useful in the treatment of neuroprotection and in the treatment of neurodegeneration following stroke, cardiac arrest, pulmonary bypass, traumatic brain injury, spinal cord injury or the like.

The compounds of Formula I are also useful in the treatment of tinnitus.

The compounds of Formula I are also useful in preventing or reducing dependence on, or preventing or reducing tolerance or reverse tolerance to, a dependence—inducing agent. Examples of dependence inducing agents include opioids (e.g. morphine), CNS depressants (e.g. ethanol), psychostimulants (e.g. cocaine) and nicotine.

The compounds of Formula I are also useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of Formula I are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

The compounds of Formula I are also useful in the treatment of a neoplasia that produces a prostaglandin in a subject in need of such treatment. The term "a neoplasia that produces a prostaglandin" includes brain cancer, bone cancer, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that effect epithelial cells throughout the body. Preferably, neoplasia is selected from gastrointestinal cancer, liver cancer, bladder cancer, pancreas cancer, ovary cancer, prostate cancer, cervical cancer, lung cancer, breast cancer and skin cancer, such as squamus cell and basal cell cancers.

It is to be understood that reference to treatment includes both treatment of established symptoms and prophylactic treatment, unless explicitly stated otherwise.

Dose Ranges

The magnitude of prophylactic or therapeutic dose of a compound of Formula I will, of course, vary with the nature and severity of the condition to be treated, and with the particular compound of Formula I used and its route of administration. The dose will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.01 mg to about 25 mg (preferably from 0.1 mg to about 10 mg) of a compound of Formula I per kg of body weight per day.

In the case where an oral composition is employed, a suitable dosage range is, e.g. from about 0.01 mg to about 100 mg of a compound of Formulas I or I a per kg of body weight per day, preferably from about 0.1 mg to about 10 mg per kg.

For use where a composition for sublingual administration is employed, a suitable dosage range is from 0.01 mg to about 25 mg (preferably from 0.1 mg to about 5 mg) of a compound of Formula I per kg of body weight per day.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, sublingual, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, sublingual, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: COX-2 inhibitors, such as celecoxib, rofecoxib, etoricoxib, valdecoxib or parecoxib; 5-lipoxygenase inhibitors; NSAIDs, such as diclofenac, indomethacin, nabumetone or ibuprofen; leukotriene receptor antagonists; DMARDs such as methotrexate; adenosine A1 receptor agonists; sodium channel blockers, such as lamotrigine; NMDA receptor modulators, such as glycine receptor antagonists; gabapentin and related compounds; tricyclic antidepressants such as amitriptyline; neurone stabilising antiepileptic drugs; monoaminergic uptake inhibitors such as venlafaxine; opioid analgesics; local anaesthetics; 5HT agonists, such as triptans, for example sumatriptan, naratriptan, zolmitriptan, eletriptan, frovatriptan, almotriptan or rizatriptan; EP1 receptor ligands; EP2 receptor ligands; EP3 receptor ligands; EP1 antagonists; EP2 antagonists and EP3 antagonists. When the compounds are used in combination with other therapeutic agents, the compounds may be administered either sequentially or simultaneously by any convenient route.

The invention thus provides, in a further aspect, a combination comprising a compound of Formula I or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

The weight ratio of the compound of the Formula I to the second active ingredient may be varied and will depend upon the effective dose of each ingredient. Generally, an effective dose of each will be used. Thus, for example, when a compound of Formula I is combined with an NSAID the weight ratio of the compound of Formula I to the NSAID will generally range from about 1000:1 to about 1:1000, preferably about 200:1 to about 1:200. Combinations of a compound of Formula I and other active ingredients will generally also be within the aforementioned range, but in each case, an effective dose of each active ingredient should be used.

Assays for Determining Biological Activity

The compounds of Formula I can be tested using the following assays to determine their prostanoid antagonist or agonist activity in vitro and in vivo and their selectivity. The prostaglandin receptor activities demonstrated are DP, $EP_1$, $EP_2$, $EP_3$, $EP_4$, FP, IP and TP.

Stable Expression of Prostanoid Receptors in the Human Embryonic Kidney (HEK) 293(ebna) Cell Line Prostanoid receptor cDNAs corresponding to full length coding sequences are subcloned into the appropriate sites of mammalian expression vectors and transfected into HEK 293 (ebna) cells. HEK 293(ebna) cells expressing the individual cDNAs are grown under selection and individual colonies are isolated after 2-3 weeks of growth using the cloning ring method and subsequently expanded into clonal cell lines.

Prostanoid Receptor Binding Assays

Transfected HEK 293(ebna) cells are maintained in culture, harvested and membranes are prepared by differential centrifugation, following lysis of the cells in the presence of protease inhibitors, for use in receptor binding assays. Prostanoid receptor binding assays (for DP1, DP2 (CRTH2), EP 1, EP2, EP3-11, EP4, FP, IP, and TP) are performed in 10 mM MES/KOH (pH 6.0) (EPs, FP and TP) or 10 mM HEPES/KOH (pH 7.4) (DPs and IP), containing 1 mM EDTA, 2.5-30 mM divalent cation and the appropriate radioligand. Synthetic compounds are added in dimethylsulfoxide which is kept constant at 1% (v/v) in all incubations. The reaction is initiated by addition of membrane protein. Non-specific binding is determined in the presence of 10 μM of the corresponding non-radioactive prostanoid. Incubations are conducted for 60-90 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves. The binding affinity of the compounds is determined by calculating the equilibrium inhibition constant ($K_i$) from the equation $K_i = \text{InPt}/1 + [\text{radioligand}]/K_d$ where $K_d$ is the equilibrium dissociation constant for the radioligand:receptor interaction and InPt is the inflection point of the dose-response curves.

Examples 1 to 22 and 33 to 80 were tested in the above binding assay for the EP4 receptor and demonstrated $IC_{50}$s of less than 100 nM. Representative data is provided in the following table:

| Example | Potency in Binding Assay (nM) |
|---|---|
| 1 | 0.47 |
| 7 | 0.42 |
| 19 | 0.72 |
| 33 | 0.83 |
| 39 | 0.76 |
| 63 | 0.61 |

Prostanoid Receptor Agonist and Antagonist Assays

Whole cell second messenger assays measuring stimulation of intracellular cAMP accumulation in HEK-293(ebna)-hEP4 cells are performed to determine whether receptor ligands are agonists or antagonists. Cells are harvested and resuspended in HBSS containing 25 mM HEPES, pH 7.4. Incubations contain 0.5 mM IBMX (phosphodiesterase inhibitor, available from Biomol). Samples are incubated at 37° C. for 10 min, the reaction is terminated and cAMP levels are then measured. Ligands are added in dimethylsulfoxide which is kept constant at 1% (v/v; agonists) or 2% (v/v; antagonists) in all incubations. For agonists, second messenger responses are expressed as a function of ligand concentration and both $EC_{50}$ values and the maximum response as compared to a $PGE_2$ standard are calculated. For antagonists, the ability of a ligand to inhibit an agonist response is determined by carrying out dose-response curves in the presence of $PGE_2$ agonist at a concentration corresponding to its $EC_{70}$. $IC_{50}$ values are calculated as the concentration of ligand required to inhibit 50% of the $PGE_2$-induced activity.

In the EP4 receptor antagonist assay, representative examples were tested and demonstrated $EC_{50}$s of less than 100 nM.

Rat Paw Edema Assay

The method is the same as described in Chan et al (J. Pharmacol. Exp. Ther. 274: 1531-1537, 1995).

Acute Inflammatory Hyperalgesia Induced by Carrageenan in Rats

The method is the same as described in Boyce et al (Neuropharmacology 33: 1609-1611, 1994).

Adjuvant-Induced Arthritis in Rats

Female Lewis rats (body weight ~146-170 g) are weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10-3.0 mg/kg) such that the body weights were equivalent within each group. Six groups of 10 rats each are injected into a hind paw with 0.5 mg of *Mycobacterium butyricum* in 0.1 mL of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) are determined before (day −1) and 21 days following adjuvant injection, and primary paw volumes are determined before (day −1) and on days 4 and 21 following adjuvant injection. The rats are anesthetized with an intramuscular injection of 0.03-0.1 mL of a combination of Ketamine (87 mg/kg) and Xylazine (13 mg/kg) for radiographs and injection of adjuvant. The radiographs are made of both hind paws on day 0 and day 21 using the Faxitron (45 kVp, 30 seconds) and Kodak X-OMAT TL film, and are developed in an automatic processor. Radiographs are evaluated for changes in the soft and hard tissues by an investigator who was blinded to experimental treatment. The following radiographic changes are graded numerically according to severity: increased soft issue volume (0-4), narrowing or widening of joint spaces (0-5) subchondral erosion (0-3), periosteal reaction (0-4), osteolysis (0-4) subluxation (0-3), and degenerative joint changes (0-3). Specific criteria are used to establish the numerical grade of severity for each radiographic change. The maximum possible score per foot was 26. A test compound at total daily doses of 0.1, 0.3, 1, and 3 mg/kg/day, indomethacin at a total daily dose of 1 mg/kg/day, or vehicle (0.5% methocel in sterile water) are administered per os b.i.d. beginning post injection of adjuvant and continuing for 21 days. The compounds are prepared weekly, refrigerated in the dark until used, and vortex mixed immediately prior to administration.

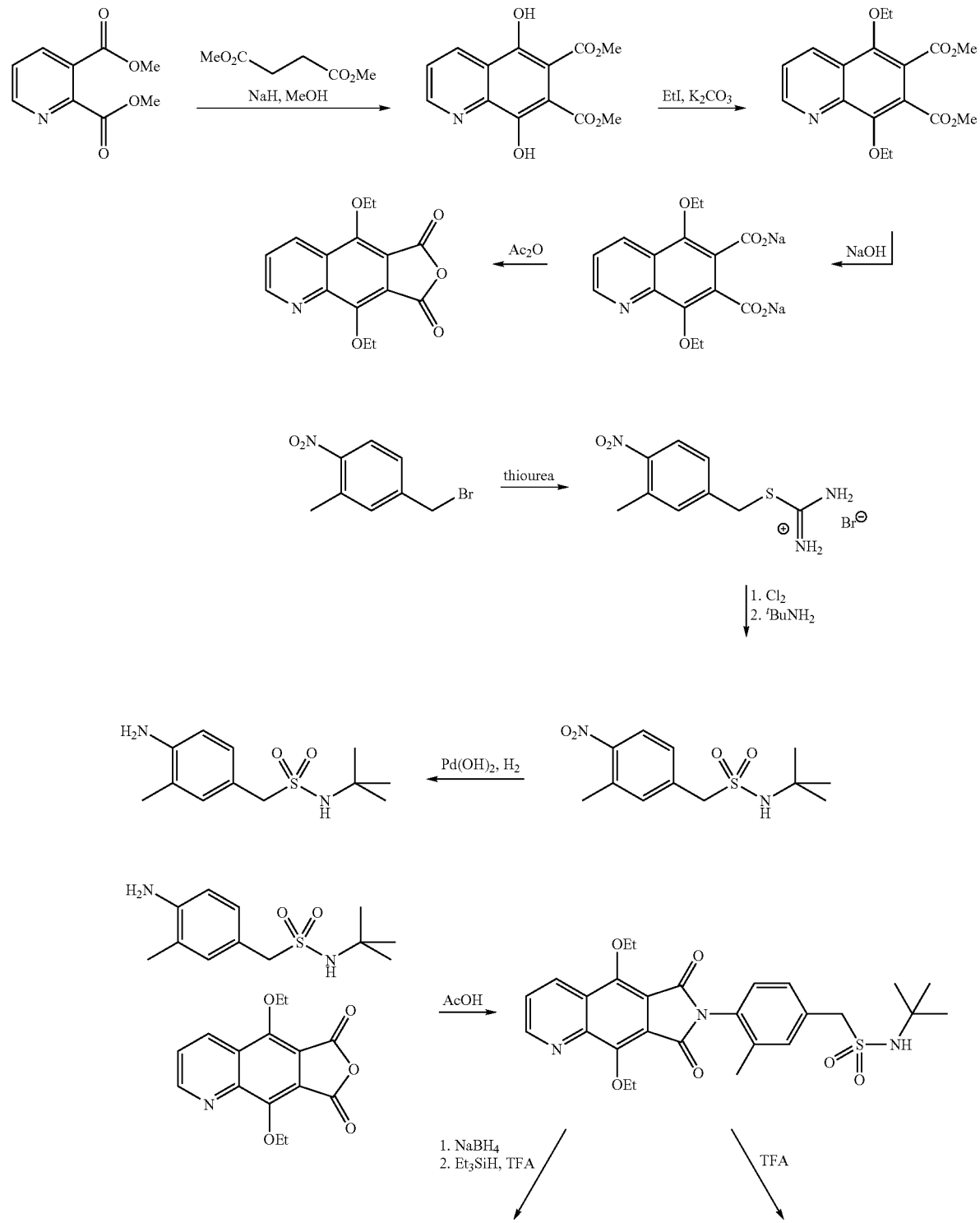

Method of Synthesis 15          16

-continued

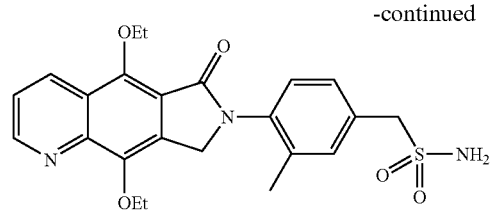 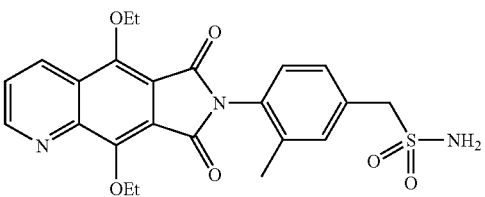

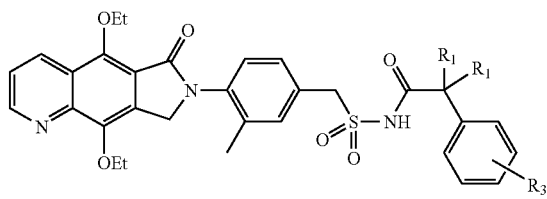

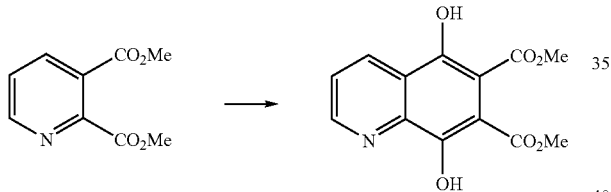

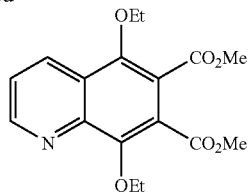

EXAMPLE 1

N-{[4-(5,9-diethoxy-6-oxo-6,8-dihydro-7H-pyrrolo[3,4-g]quinolin-7-yl)-3-methylbenzyl]sulfonyl}-2-(2-methoxyphenyl)acetamide

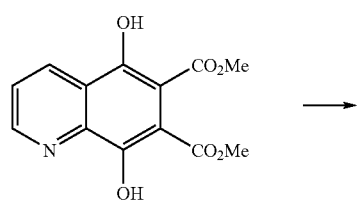

To a solution of the pyridine diester (50 g, 256 mmol) in toluene (400 mL) was added dimethyl succinate (40.4 mL, 307 mmol, 1.2 equiv) followed by sodium hydride (60% in mineral oil, 22.5 g, 307 mmol, 2.2 equiv) portionwise. Methanol (2.1 mL, 51.2 mmol, 0.2 equiv) was then added slowly and the mixture was heated to reflux for 2 hours, during which time a bright red precipitate separated from the solution. The mixture was then cooled to rt, and the reaction was quenched by the addition of 180 mL of 4 N HCl(aq). The biphasic mixture was diluted with CH$_2$Cl$_2$ (500 mL) and H$_2$O (500 mL), the layers separated, and the aqueous phase further extracted with CH$_2$Cl$_2$ (3×500 mL). The combined organic fractions were dried (Na$_2$SO$_4$) and concentrated in vacuo, then the resulting solid was triturated with 500 mL Et$_2$O to provide 28.6 g (103 mmol, 40%) of the desired product as a yellow solid. MS: m/z=278.0 [M+H]

-continued

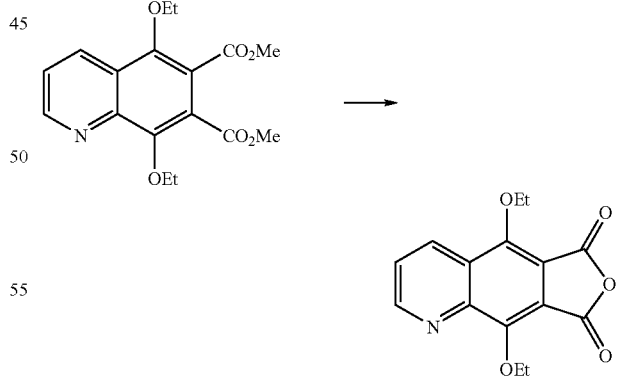

To a solution of the diphenol (12.0 g, 43.3 mmol) in DMF (80 mL) was added iodoethane (8.73 mL, 108 mmol, 2.5 equiv) and K$_2$CO$_3$ (13.2 g, 95.3 mmol, 2.2 equiv). The mixture was heated to 70° C. for four hours, then cooled to rt and poured into 1000 mL H$_2$O. The resulting grey solid was removed by filtration, air dried then dried under high vacuum for 12 hours to provide 10.5 g (31.4 mmol, 73%) of the desired product as a grey solid. MS: m/z=334.0 [M+H]

To a solution of the diester (28.8 g, 86.4 mmol) in 2:1 THF:MeOH (1.2 L) was added 70 mL 10 N NaOH(aq), and the mixture was heated to 55° C. for 1 hour, during which time a white precipitate formed. After cooling to rt, the solid (which is the disodium dicarboxylate) was removed by filtration and rinsed with THF (3×50 mL) and dried under high vacuum for 1 hour then used directly. The dicarboxylate was suspended in Ac$_2$O (250 mL) and the mixture heated to reflux for 2 hours. After cooling to rt, the suspended solid (NaOAc)

was removed by filtration, and the solvent was removed in vacuo to provide 23 g (79.9 mmol, 92%) of the anhydride as a fluffy, light brown solid.

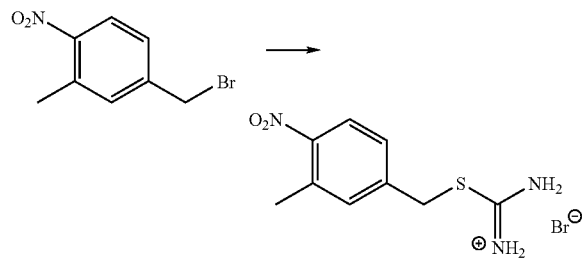

To a suspension of the bromide (30 g, 130 mmol) in EtOH (70 mL) was added thiourea (9.9 g, 130 mmol) and the mixture was heated to reflux for 20 hours. After cooling to rt, the mixture was poured into 300 mL Et₂O and the resulting solid was removed by filtration and rinsed with Et₂O (2×50 mL) to provide 38.6 g (126 mmol, 97%) pure product as a fluffy, white solid.

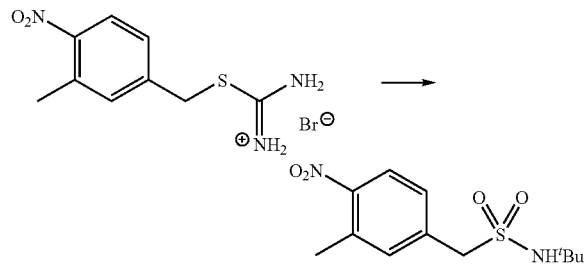

A suspension of the HBr salt (38.6 g, 126 mmol) in 1:1 CH₂Cl₂:H₂O (600 mL) was cooled to 0° C. then chlorine gas was bubbled in to the mixture at such a rate that the internal temperature was maintained below 10° C. Once the exotherm had ceased, bubbling was continued at a low rate for 2 hours, then the biphasic mixture was poured into 300 mL 10% Na₂S₂O₃(aq). Once the initial exothermic quench had subsided, the mixture was transferred to a separatory funnel, the organic layer removed, and the aqueous phase extracted with a further 2×200 mL of CH₂Cl₂. The combined organic fractions were dried (Na₂SO₄) and concentrated in vacuo, then the resulting brown oil was diluted with CH₂Cl₂ (300 mL). Tert-butylamine (67 mL, 630 mmol, 5 equiv) was then added dropwise, and the resulting mixture was stirred for 1 hour at rt then concentrated in vacuo. The resulting oily solid was triturated first with H₂O (300 mL) then hexanes (300 mL) to provide 19.5 g (68 mmol, 54%) of the desired sulfonamide as a orange solid. MS: m/z=285.0 [M–H]

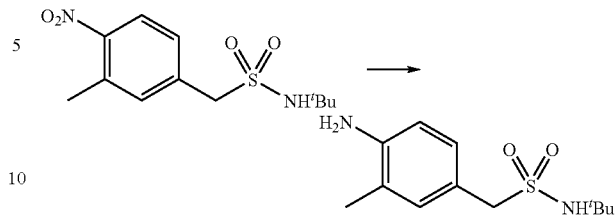

To a solution of the nitroarene (20.0 g, 73.7 mmol) in 10:1 EtOAc:EtOH (220 mL) was added Pd(OH)₂ (20 wt %, 200 mg) and the reaction vessel was evacuated and backfilled with N₂ three times. The vessel was then charged with 50 psi of H₂ and shaken vigorously for 2 hours. The catalyst was deactivated by the addition of CH₂Cl₂ (30 mL) and then the mixture was filtered through Celite. Concentration in vacuo provided 17.8 g (73.7 mmol, 100%) of pure aniline as a yellow solid.

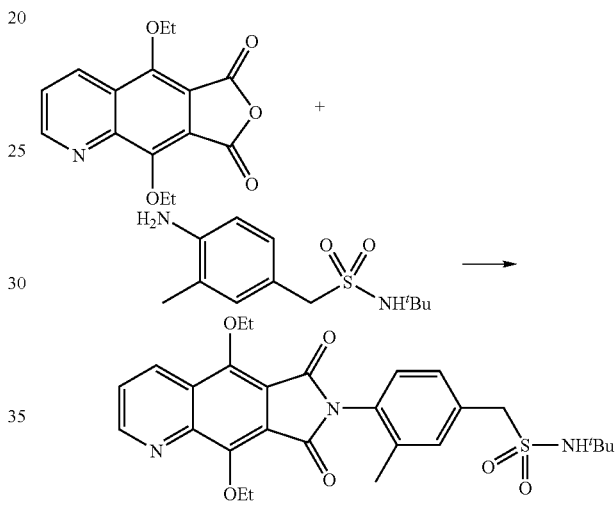

A suspension of the anhydride (18.7 g, 65 mmol) and the aniline (21.7 g, 84.5 mmol, 1.3 equiv) in AcOH (500 mL) was heated to reflux for 17 hours, then cooled to rt and concentrated in vacuo. The resulting brown oil was purified directly by flash column chromatography (70:30 to 10:90 hexanes: EtOAc; linear gradient) to provide 25.0 g (48 mmol, 74%) of the desired succinamide as a yellow foam. MS: m/z=526.1 [M+H]

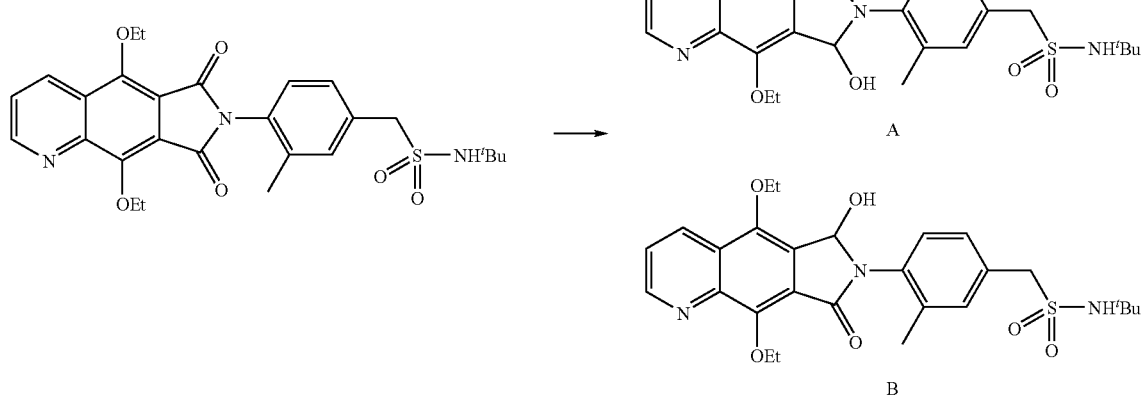

A solution of the succinamide (23 g, 43.8 mmol) in 1:1 THF/MeOH (880 mL) was cooled to 0° C. and NaBH₄ (2.49 g, 65.7 mmol, 1.5 equiv) was added in a single portion. After stirring for 1 hour at 0° C., the reaction was quenched by the addition of sat. NH₄Cl(aq) (400 mL) and the organic solvents were removed in vacuo. The residue was diluted with 300 mL of H₂O, and extracted with CH₂Cl₂ (3×300 mL). The combined organic extracts were dried (Na₂SO₄) and concentrated in vacuo to provide a 1.2:1 mixture of A:B which was used directly in the subsequent step without further purification. MS: m/z=528.1 [M+H]

concentration in vacuo. Combined yield: 17.2 g (37.7 mmol, 86%). MS: m/z=456.1 [M+H]

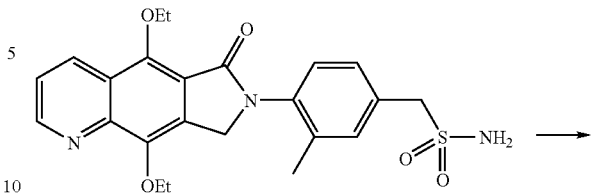

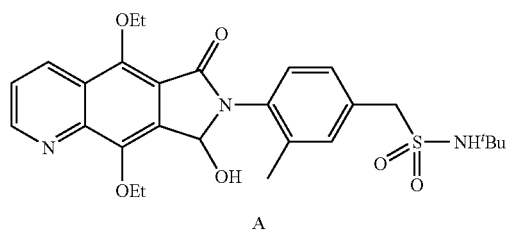

A

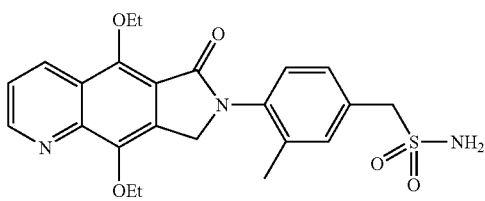

C

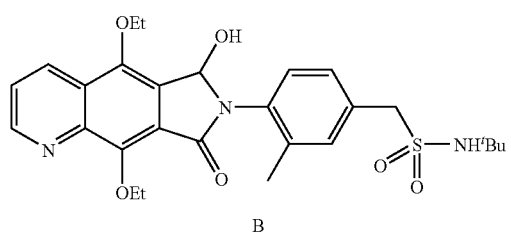

B

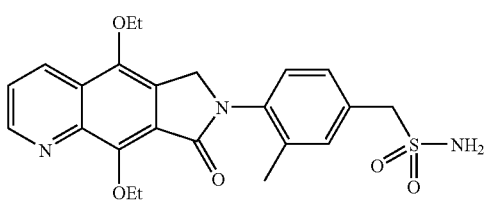

D

To a solution of the mixture of animals (43.8 mmol) in CH₂Cl₂ (100 mL) was added TFA (150 mL), resulting in the formation of a dark green solution. Triethylsilane (35 mL, 219 mmol, 5 equiv) was added, and the mixture was stirred for 13 hours at rt, during which time the color changed to light orange. The mixture was then concentrated in vacuo, then rediluted with 150 mL TFA and stirred for 4 hours to ensure complete deprotection of the ᵗbutyl groups. The mixture was then again concentrated in vacuo, diluted with CH₂Cl₂ (500 mL) and swirled with 10% NH₄OH(aq) (500 mL) for 5-10 minutes. The layers were separated, and the aqueous phase was further extracted with 2×150 mL of CH₂Cl₂. The combined organic fractions were dried (Na₂SO₄), the fine solid suspended in this layer (pure isomer D) was removed by filtration through celite and the solvent was removed in vacuo. ¹H NMR analysis at this stage revealed a 3:1 mixture of isomer C:D. Purification by flash column chromatography (20:80 to 0:100 hexanes:EtOAc; linear gradient) provided 9.2 g (20.1 mmol, 46%) of the faster eluting isomer (C) and 3.0 g (6.6 mmol, 33%) of the slower eluting isomer (D). Further quantities of isomer D (5.0 g, 10.9 mmol 25%) can be obtained by stirring the celite mixture in 1:1 CH₂Cl₂:MeOH (300 mL) overnight, removing the celite by filtration and -continued

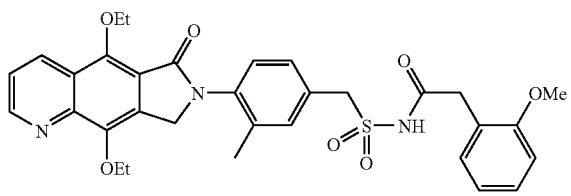

To a suspension of the sulfonamide (8.0 g, 17.6 mmol) in CH₂Cl₂ (250 mL) was added 2-methoxyphenylacetic acid (8.8 g, 52.7 mmol, 3 equiv), EDC (10.1 g, 52.7 mmol, 3 equiv) and DMAP (6.44 g, 52.7 mmol, 3 equiv), and the mixture was heated to reflux for 20 hours. After cooling to rt, AcOH (10 mL) was added, and the mixture was poured into H₂O (400 mL) and extracted with CH₂Cl₂ (3×250 mL). The combined organic fractions were dried (Na₂SO₄) and concentrated in vacuo. Purification by flash column chromatography (70:30 to 0:100 hexanes:EtOAc; linear gradient) provided 10.0 g (16.5 mmol, 94%) of pure acylsulfonamide as a light yellow foam. MS: m/z=604.2 [M+H]

Following the method of Example 1, the compounds of Table 1 were prepared.

Table 1

| Example | Name | Structure | MS (APCI) |
|---|---|---|---|
| 2 | N-{[4-(5,9-diethoxy-6,8-dioxo-6,8-dihydro-7H-pyrrolo[3,4-g]quinolin-7-yl)benzyl]sulfonyl}-2-phenylacetamide | 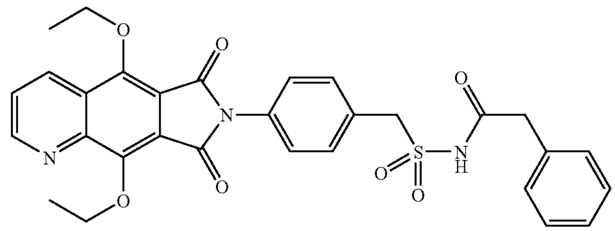 | 574.0 (M + 1) |
| 3 | N-{[4-(5,9-diethoxy-6-oxo-6,8-dihydro-7H-pyrrolo[3,4-g]quinolin-7-yl)benzyl]sulfonyl}-2-phenylacetamide | 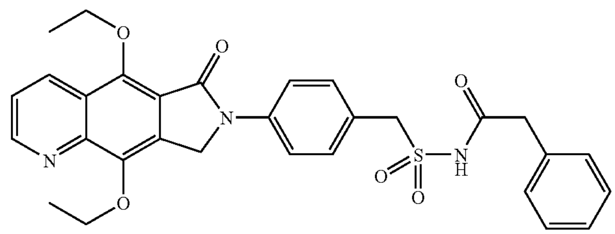 | 560.1 (M + 1) |
| 4 | N-{[4-(5,9-diethoxy-6,8-dioxo-6,8-dihydro-7H-pyrrolo[3,4-g]quinolin-7-yl)-3-methylbenzyl]sulfonyl}-2-phenylacetamide | 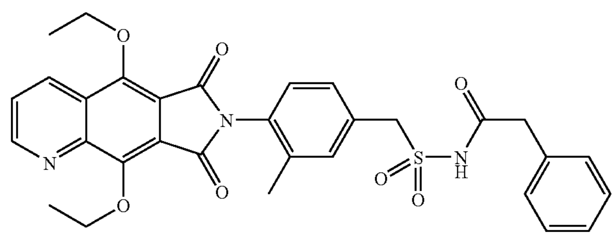 | 588.2 (M + 1) |
| 5 | N-{[4-(5,9-diethoxy-6-oxo-6,8-dihydro-7H-pyrrolo[3,4-g]quinolin-7-yl)-3-methylbenzyl]sulfonyl}-2-phenylacetamide | 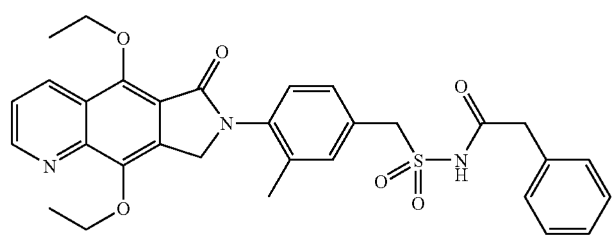 | 572.2 (M + 1) |
| 6 | N-{[4-(5,9-diethoxy-6-oxo-6,8-dihydro-7H-pyrrolo[3,4-g]quinolin-7-yl)-3-methylbenzyl]sulfonyl}-2-phenylpropanamide | 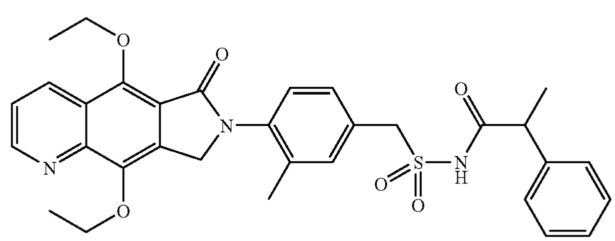 | 586.3 (M − 1) |
| 7 | N-{[4-(5,9-diethoxy-6-oxo-6,8-dihydro-7H-pyrrolo[3,4-g]quinolin-7-yl)-3-methylbenzyl]sulfonyl}-2-[2-(trifluoromethyl)phenyl]acetamide | 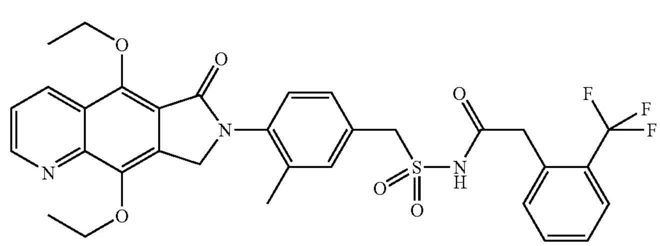 | 642.1 (M + 1) |

Table 1-continued

| Example | Name | Structure | MS (APCI) |
|---|---|---|---|
| 8 | N-{[4-(5,9-diethoxy-6-oxo-6,8-dihydro-7H-pyrrolo[3,4-g]quinolin-7-yl)-3-methylbenzyl]sulfonyl}-2-(2-fluorophenyl)acetamide | 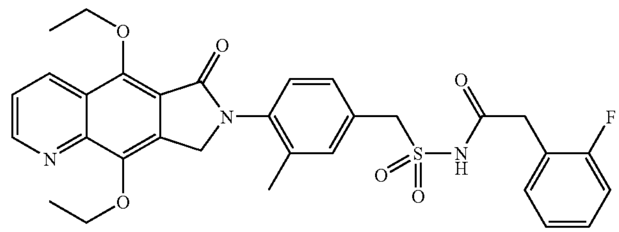 | 592.0 (M + 1) |
| 9 | N-{[4-(5,9-diethoxy-6-oxo-6,8-dihydro-7H-pyrrolo[3,4-g]quinolin-7-yl)-3-methylbenzyl]sulfonyl}-2-pyridin-4-ylacetamide | 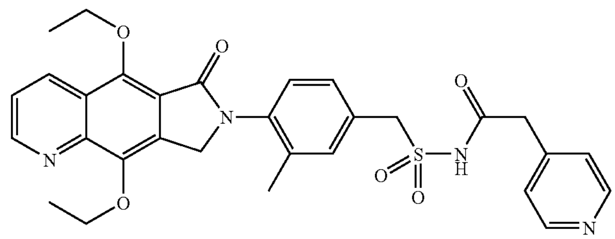 | 576.2 (M + 1) |
| 10 | N-{[4-(5,9-diethoxy-6-oxo-6,8-dihydro-7H-pyrrolo[3,4-g]quinolin-7-yl)-3-methylbenzyl]sulfonyl}-2-pyridin-3-ylacetamide | 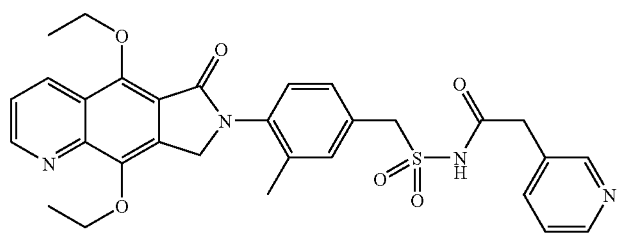 | 576.0 (M + 1) |
| 11 | N-{[4-(5,9-diethoxy-6-oxo-6,8-dihydro-7H-pyrrolo[3,4-g]quinolin-7-yl)-3-methylbenzyl]sulfonyl}-2-pyridin-2-ylacetamide | 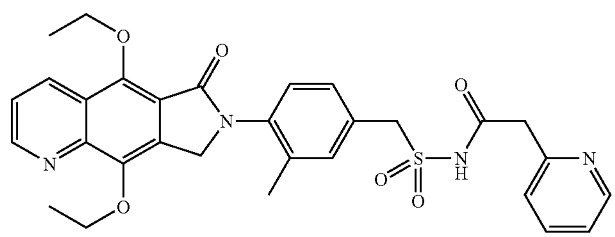 | 576.4 (M + 1) |
| 12 | 2-(2-chlorophenyl)-N-{[4-(5,9-diethoxy-6-oxo-6,8-dihydro-7H-pyrrolo[3,4-g]quinolin-7-yl)-3-methylbenzyl]sulfonyl}acetamide | 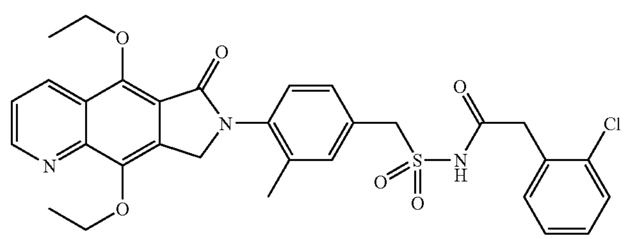 | 608.1 (M + 1) |
| 13 | N-{[3-bromo-4-(5,9-diethoxy-6,8-dioxo-6,8-dihydro-7H-pyrrolo[3,4-g]quinolin-7-yl)benzyl]sulfonyl}-2-(2-methoxyphenyl)acetamide | 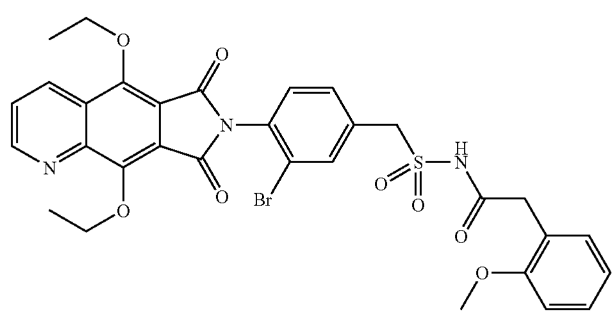 | 684.2, 682.2 (M + 1) |

Table 1-continued

| Example | Name | Structure | MS (APCI) |
|---|---|---|---|
| 14 | N-{[3-bromo-4-(5,9-diethoxy-6,8-dioxo-6,8-dihydro-7H-pyrrolo[3,4-g]quinolin-7-yl)benzyl]sulfonyl}-2-phenylacetamide | 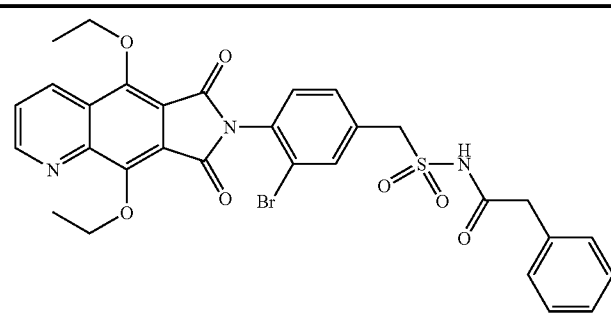 | 652.1, 650.1 (M + 1) |
| 15 | N-{[4-(5,9-diethoxy-6-oxo-6,8-dihydro-7H-pyrrolo[3,4-g]quinolin-7-yl)-3-methylbenzyl]sulfonyl}-1-phenylcyclopropanecarboxamide | 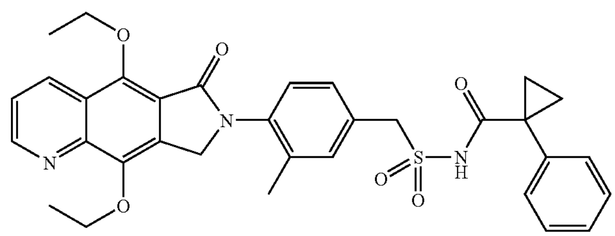 | 600.2 (M + 1) |
| 16 | N-{[4-(5,9-diethoxy-6-oxo-6,8-dihydro-7H-pyrrolo[3,4-g]quinolin-7-yl)-3-methylbenzyl]sulfonyl}-2-[2-(trifluoromethoxy)phenyl]acetamide | 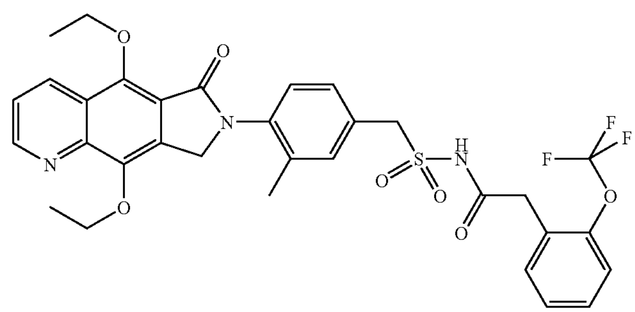 | 656.1 (M − 1) |
| 17 | N-{[4-(5,9-diethoxy-6-oxo-6,8-dihydro-7H-pyrrolo[3,4-g]quinolin-7-yl)-3-methylbenzyl]sulfonyl}-2-(2,5-dimethoxyphenyl)acetamide | 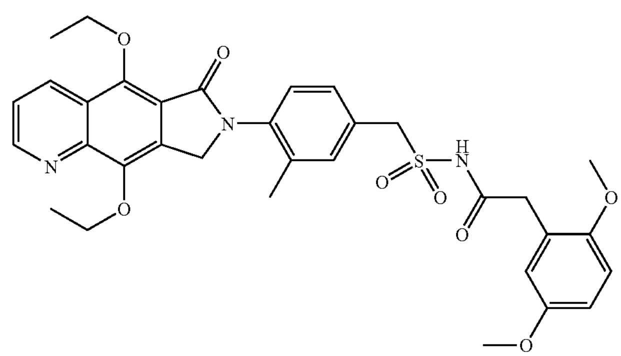 | 632.2 (M − 1) |
| 18 | 2-(5-bromo-2-methoxyphenyl)-N-{[4-(5,9-diethoxy-6-oxo-6,8-dihydro-7H-pyrrolo[3,4-g]quinolin-7-yl)-3-methylbenzyl]sulfonyl}acetamide | 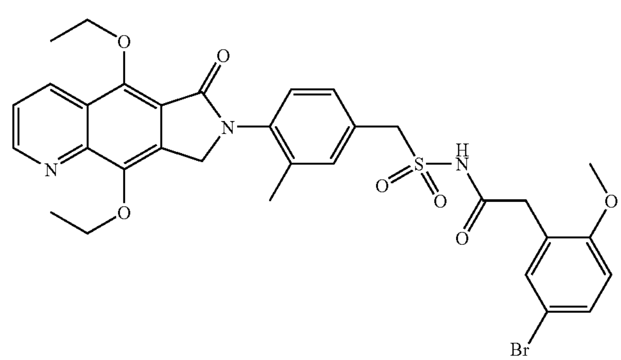 | 682.1, 680.1 (M − 1) |

Table 1-continued

| Example | Name | Structure | MS (APCI) |
|---|---|---|---|
| 19 | N-{[4-(5,9-diethoxy-6-oxo-6,8-dihydro-7H-pyrrolo[3,4-g]quinolin-7-yl)-3-methylbenzyl]sulfonyl}-2-(1-naphthyl)acetamide | 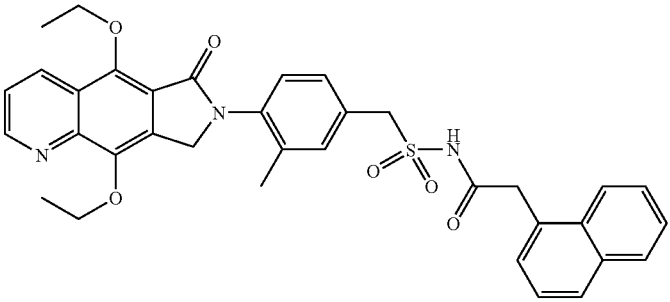 | 622.1 (M − 1) |
| 20 | N-{[4-(5,9-diethoxy-8-oxo-6,8-dihydro-7H-pyrrolo[3,4-g]quinolin-7-yl)benzyl]sulfonyl}-2-phenylacetamide | 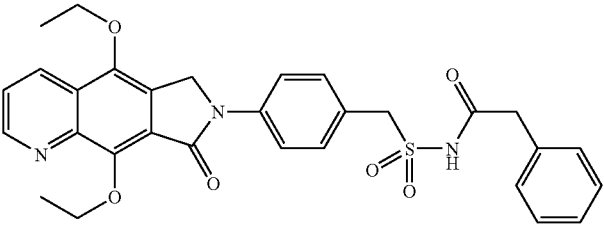 | 560.1 (M + 1) |
| 21 | N-{[4-(5,9-diethoxy-8-oxo-6,8-dihydro-7H-pyrrolo[3,4-g]quinolin-7-yl)-3-methylbenzyl]sulfonyl}-2-phenylacetamide | 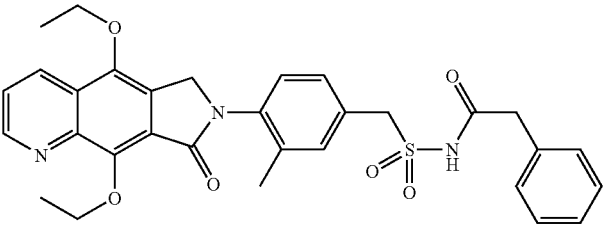 | 572.2 (M + 1) |

The compounds of Table 2 further exemplify the invention:

TABLE 2

| Example | Name | Structure |
|---|---|---|
| 22 | N-{[4-(5,9-diethoxy-6-oxo-6,8-dihydro-7H-pyrrolo[3,4-g]quinolin-7-yl)-3-methylbenzyl]sulfonyl}-1-(2-methoxyphenyl)cyclopropane-carboxamide | 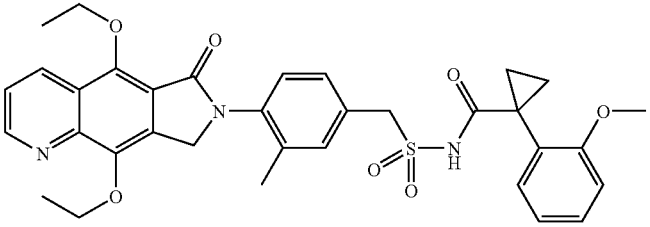 |
| 23 | N-{[4-(5,9-diisopropoxy-6-oxo-6,8-dihydro-7H-pyrrolo[3,4-g]quinolin-7-yl)-3-methylbenzyl]sulfonyl}-2-(2-methoxyphenyl)acetamide | 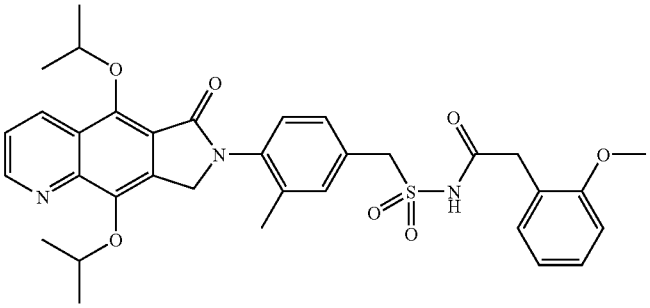 |

TABLE 2-continued

| Example | Name | Structure |
|---|---|---|
| 24 | 2-(2-methoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)propanamide | 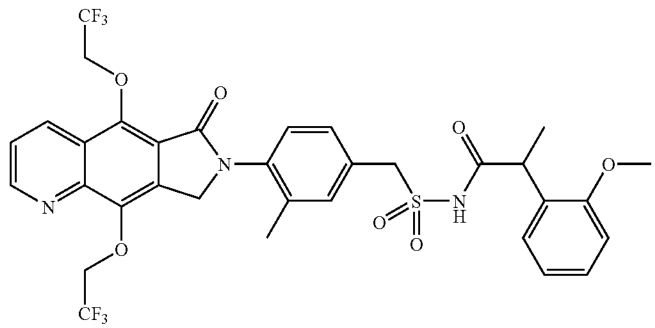 |
| 25 | N-({4-[5,9-bis(cyclopropyloxy)-6-oxo-6,8-dihydro-7H-pyrrolo[3,4-g]quinolin-7-yl]-3-methylbenzyl}sulfonyl)-2-(2-methoxyphenyl)acetamide | 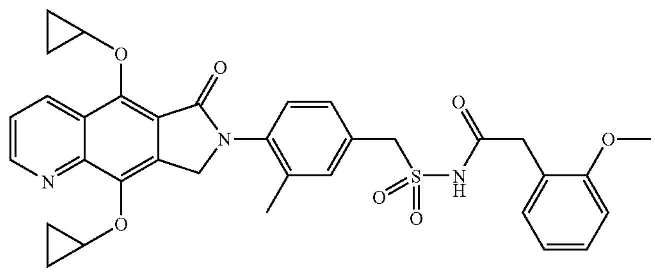 |
| 26 | N-{[3-bromo-4-(5,9-diethoxy-6-oxo-6,8-dihydro-7H-pyrrolo[3,4-g]quinolin-7-yl)benzyl]sulfonyl}-2-methyl-2-(1-naphthyl)propanamide | 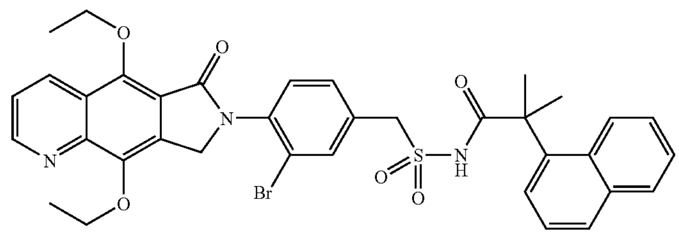 |
| 28 | N-{[4-(5,9-diisopropyl-6-oxo-6,8-dihydro-7H-pyrrolo[3,4-g]quinolin-7-yl)-3-methylbenzyl]sulfonyl}-2-(2-fluorophenyl)acetamide | 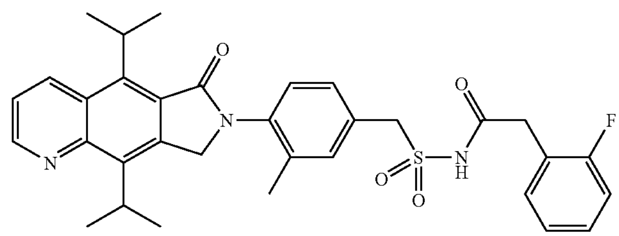 |
| 29 | N-{[3-cyano-4-(5,9-dicyclopropyl-6-oxo-6,8-dihydro-7H-pyrrolo[3,4-g]quinolin-7-yl)benzyl]sulfonyl}-2-pyridin-2-ylacetamide | 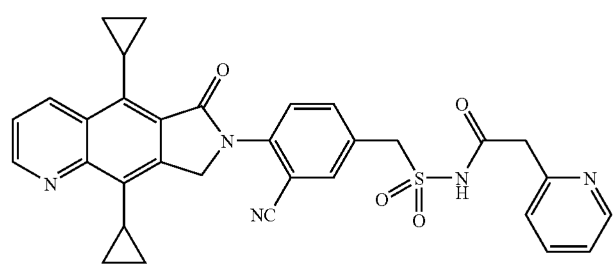 |
| 30 | N-{[4-(5-ethoxy-9-isopropoxy-6-oxo-6,8-dihydro-7H-pyrrolo[3,4-g]quinolin-7-yl)-3-methylbenzyl]sulfonyl}-2-pyridin-2-ylpropanamide | 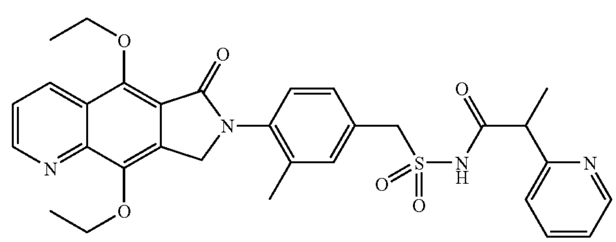 |

TABLE 2-continued

| Example | Name | Structure |
|---|---|---|
| 31 | N-({3-methyl-4-[6-oxo-5,9-bis(trifluoromethoxy)-6,8-dihydro-7H-pyrrolo[3,4-g]quinolin-7-yl]benzyl}sulfonyl)-2-pyridin-2-ylacetamide | 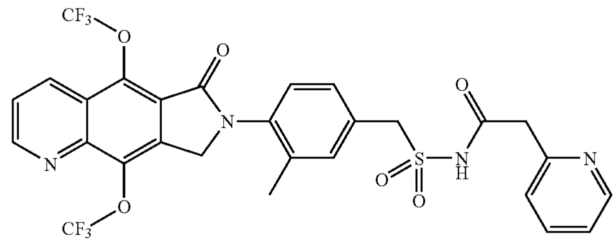 |
| 32 | N-({4-[5,9-bis(difluoromethoxy)-6-oxo-6,8-dihydro-7H-pyrrolo[3,4-g]quinolin-7-yl]-3-methylbenzyl}sulfonyl)-2-(2-chloro-5-fluorophenyl)-2-methylpropanamide | 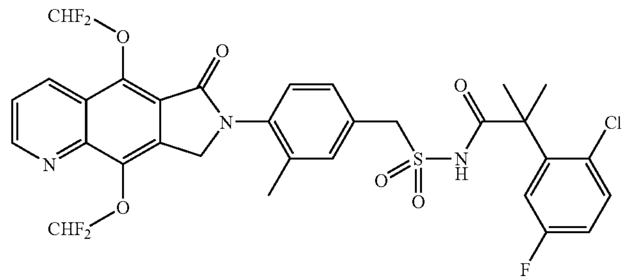 |

PREPARATIVE EXAMPLE 1

1-(4-Amino-3-methylphenyl)methanesulfonamide 15

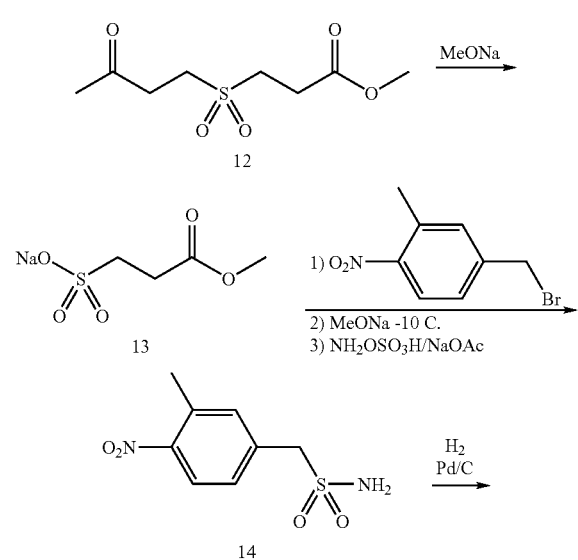

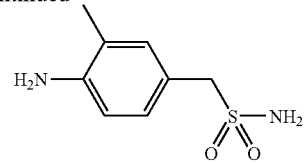

Step 1: Methyl 3-[(3-oxobutyl)thio]propanoate 11

Methyl vinyl ketone (90%, 185 ml, 2.0 mol) was added portionwise to a solution of methyl 3-mercaptopropionate (200 ml, 1.83 mol) and triethylamine (26 ml, 0.1 equiv) in THF (2.4 L). This mixture was heated slowly to 50 C and stirred at that temperature for 4.5 h. The solvent was then evaporated to afford 11 as an oil.

Step 2: Methyl 3-[(3-oxobutyl)sulfonyl]propanoate 12

A mixture containing 11 (348 g, 1.83 mol), sodium tungstate dihydrate (30.2 g, 0.05 equiv) and aliquat 336 (42 ml, 0.05 equiv) in water (200 ml), cyclohexane (500 ml) and EtOAc (1.0 L) was heated to 60 C. Hydrogen peroxide (673 ml of a 30% solution in water, 3.6 equiv) was then added slowly over 1.5 h (during which time the heating was halted and the reaction temperature reached 67 C) and this mixture was kept for another 3.5 h at 60 C after the end of the addition. EtOAc (1 L) and water (1 L) were then added and the phases were separated. The aqueous layer was extracted again with EtOAc (500 ml) and the organics were washed with water and brine, dried over Na$_2$SO$_4$, filtered through a small pad of silica (400 ml) and concentrated to a final volume of 1 L. Hexane (1 L) was added and the crystallized solid filtered to yield 164.3 g (40%) of 12 as a white powder.

Step 3: Sodium 3-methoxy-3-oxopropane-1-sulfonate 13

To a suspension of 12 (141 g, 636 mmol) in THF (1.2 L) and MeOH (700 ml) in an ice bath was added slowly sodium methoxide (144 ml of a 25% solution in MeOH, 1.05 equiv). At the end of the addition, the bath was removed and the mixture stirred at r.t. for 1 h. The solvents were than evaporated and the remaining solid was triturated in ether containing a small amount of EtOAc. The slightly hygroscopic white solid was filtered and dried under high vacuum o.n. to yield 108.7 g (98%) of 13.

Step 4:
1-(3-Methyl-4-nitrophenyl)methanesulfonamide 14

3-Methyl-4-nitrobenzyl bromide (60 g, 261 mmol) was added portionwise to a suspension of sodium 3-methoxy-3-oxopropane-1-sulfonate 13 (50 g, 1.1 equiv) in DMSO (400 ml) at r.t. (with occasional ice bath cooling to keep the temperature below 28 C) and this mixture was stirred at r.t. for 3 h (TLC (EtOAc/hexane 50%) indicated complete consumption of the starting material to cleanly form a new spot). MeOH (400 ml) was then added and the mixture was cooled down to −10 C. MeONa (62 ml of a 25% solution in MeOH) was added dropwise at −9 C and the reaction was warmed slowly to 0 C (where complete disappearance of the intermediate was seen by TLC). Finally, this mixture was poured portionwise into an aqueous solution containing hydroxylamine-O-sulfonic acid (118 g, 4 equiv) and NaOAc (107 g, 5 equiv) at 0 C (very exothermic reaction). The reaction was warmed very slowly to r.t. and was stirred at that temperature o.n. More water (1 L) and EtOAc (1 L) were added to dissolve the precipitate. The product was extracted into EtOAc, washed with brine and dried over $Na_2SO_4$. Evaporation of solvents gave a gummy solid, which was triturated in toluene (300 ml) for an hour to yield 49.35 g (82%) of pure 14 as a white solid.

Step 5:
1-(4-Amino-3-methylphenyl)methanesulfonamide 15

The sulfonamide 14 (31.7 g, 138 mmol) was dissolved into boiling EtOH (600 ml) containing some AcOH (80 ml). To this solution was added 10% Pd/C (1.4 g) and this mixture was stirred under hydrogen (40 psi) for 3 h. THF (50 ml) was then added and this mixture heated to dissolve the precipitated product. This solution was filtered through celite and concentrated. The resulting solid was triturated with ether:hexane 1:1 (200 ml) to yield 27.28 g (99%) of pure 15.

PREPARATIVE EXAMPLE 2

1-(2,6-Dimethoxyphenyl)cyclopropanecarboxylic Acid 19

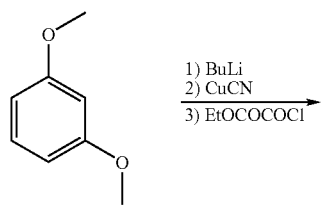

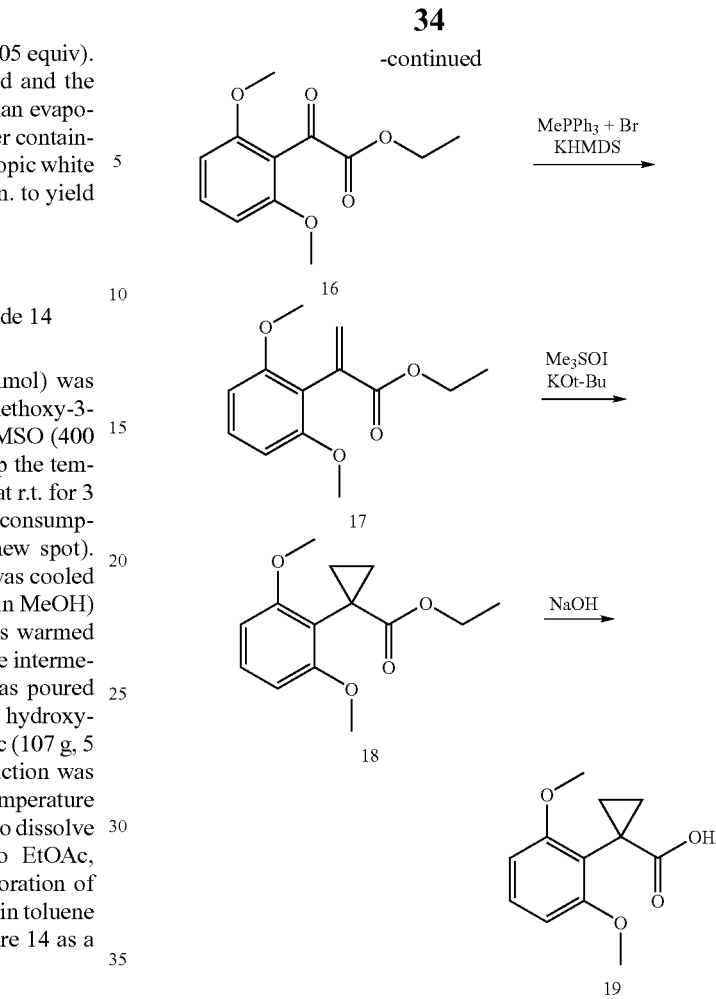

Step 1: Ethyl (2,6-dimethoxyphenyl)(oxo)acetate 16

To a mixture of resorcinol (30 ml, 229 mmol) and BuLi (109 ml of a 2.35 M solution in hexane, 1.1 equiv) at 10 C was added TMEDA (400 ul, 0.01 equiv) and this mixture was stirred at 10 C for 15 min and at r.t. o.n. to give a suspension of 1,3-dimethoxyphenyllithium (see J Organomet Chem 1997, 548, 223 for reference). A solution of CuCN (22.77 g, 1.1 equiv) and LiCl (21.1 g, 2.2 equiv) in THF (450 ml) was then added slowly to 1,3-dimethoxyphenyllithium at −78 C and this mixture was stirred for 1.5 h at that temperature. Ethyl oxalyl chloride (36 ml, 1.4 equiv) was then added rapidly at −78 C (very exothermic reaction with temperature increasing to −30 C) and the reaction was aged at −78 C for 30 min. The mixture was then warmed up slowly to 0 C and was quenched by addition of half-saturated $NH_4Cl$ (1 L) and i-PrOAc (500 ml). This mixture was filtered through celite and the product extracted into i-PrOAc. The organics were dried over $Na_2SO_4$ and concentrated. The residue was purified by filtration through silica (1 kg) with EtOAc/toluene 2.5 to 7.5% to yield 50.48 g (93%) of 16 as a yellowish oil.

Step 2: Ethyl 2-(2,6-dimethoxyphenyl)acrylate 17

To a suspension of methyltriphenylphosphonium bromide (61.1 g, 1.2 equiv) in THF (350 ml) at 0 C was added potassium bis(trimethylsilyl)amide (260 ml of a 15% solution in toluene, 1.2 equiv) and this mixture was stirred at 0 C for 15 min and at r.t. for 45 min. Then, a solution of the ketoester 16 (33.7 g, 141 mmol) in THF (70 ml) was added at 0 C and stirring was continued at r.t. for 1 h. The reaction was quenched by addition of a saturated solution of NH$_4$Cl and ice. The product was extracted into i-PrOAc and the organics were dried over Na$_2$SO$_4$ and filtered through small pad of silica. Purification of the residue by filtration through a plug of silica (1.5 L) with EtOAc/hexane 10 and 15% yielded 26.92 g (81%) of 17 as a colorless oil.

Step 3: Ethyl 1-(2,6-dimethoxyphenyl)cyclopropanecarboxylate 18

To trimethylsulfoxonium iodide (32 g, 1.2 equiv) in DMSO (250 ml) was added ground KOt-Bu (17.62 g, 1.3 equiv) and this mixture was stirred at r.t. for 30 min. A solution of the styrene 17 (28.53 g, 121 mmol) in DMSO (55 ml) was then added and this mixture was stirred at r.t. for 3 h. The reaction was poured into water (1.0 L) mixed with sat. NHCl (350 ml). The product was extracted into hexane (2×300 ml) and this solution was washed with water and brine, dried over Na$_2$SO$_4$ and filtered through silica (400 ml). The product was then eluted with EtOAc/hexane 15 and 20% to yield 18 (21.1 g, 70%) as a colorless oil.

Step 4: 1-(2,6-Dimethoxyphenyl)cyclopropanecarboxylic Acid 19

A mixture containing the ester 18 (21.11 g, 89.4 mmol) and 10 M NaOH (36 ml, 4 equiv) in THF (220 ml), MeOH (110 ml) and water (55 ml) was stirred at reflux for 4 days. Half-saturated NH$_4$Cl (600 ml) and AcOH (25 ml) were then added and the acid 19 was extracted into i-PrOAc. The organics were dried over Na$_2$SO$_4$ and concentrated. Trituration of the residue in ether:hexane 1:3 (200 ml) yielded 18.15 g (91%) of 19 as a white solid.

EXAMPLE 33

(1-(2,6-dimethoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropanecarboxamide)

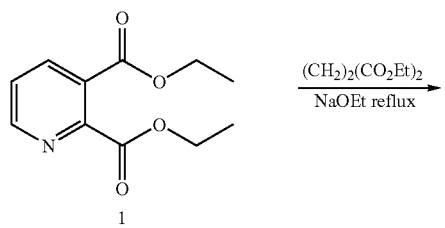

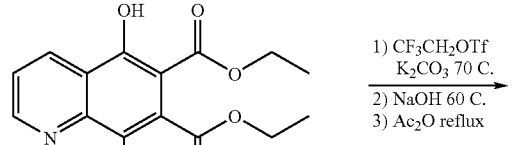

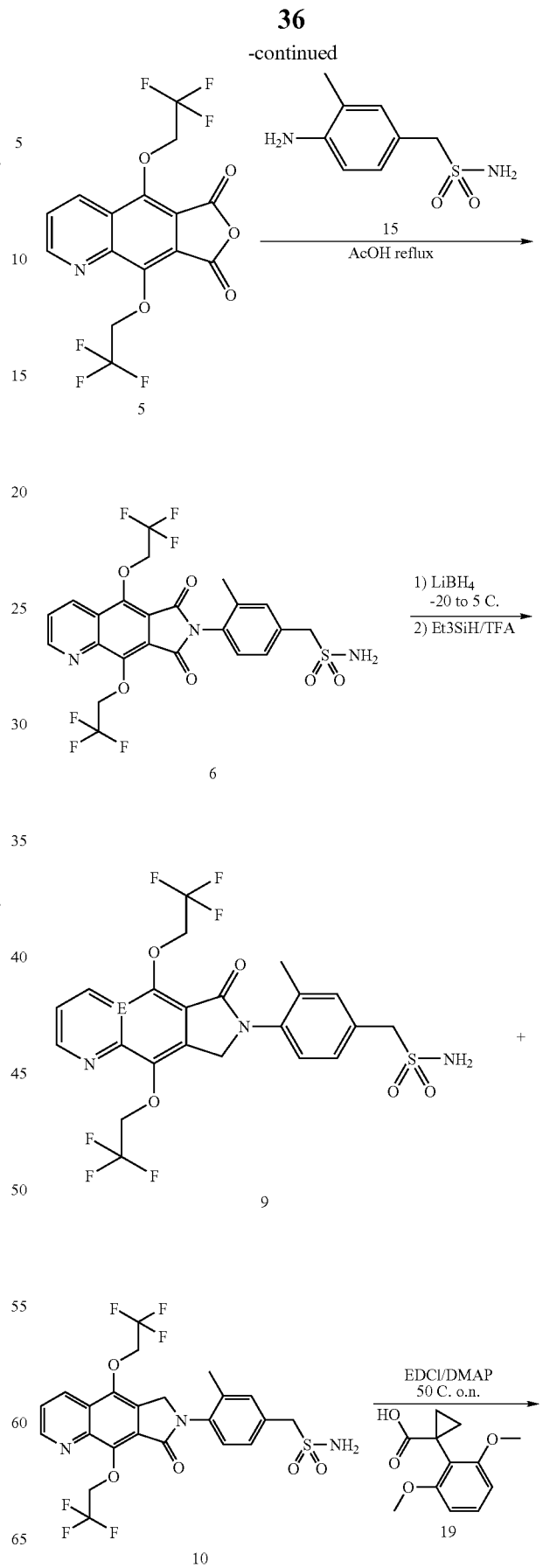

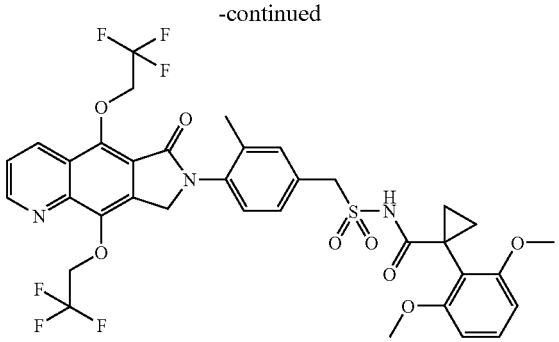

Example 33

Step 1: Diethyl pyridine-2,3-dicarboxylate 1

To a suspension of 2,3-pyridinedicarboxylic acid (200 g, 1.2 mol) in ethanol (800 ml) was added conc $H_2SO_4$ (100 ml) and this mixture was heated to reflux for 3 days (mechanical stirring). It was then cooled down to r.t. and added to crushed ice. Conc $NH_4OH$ (405 ml) was then added slowly and the pH was adjusted to 9 by addition of some aq. $NH_4Cl$. The products were extracted into i-PrOAc, dried over $Na_2SO_4$ and concentrated to yield 182.48 g of an orange oil containing 88% of the diester (60% yield), 8.1% of ethyl 3-pyridinecarboxylate and 3.5% i-PrOAc. This mixture was used as such in the next step.

Step 2: Diethyl 5,8-dihydroxyquinoline-6,7-dicarboxylate 2

To a mechanically stirred solution of diethyl pyridine-2,3-dicarboxylate 1 (86%, 85.6 g, 330 mmol) and diethyl succinate (70 ml, 414 mmol) in toluene (100 ml) at 95 C was added slowly a solution of NaOEt in EtOH (21%, 311 ml, 825 mmol) and this mixture was stirred at reflux o.n. It was then poured into an ice cold solution of sat $NH_4Cl$ (1.5 L) containing 60 ml AcOH. The products were extracted into EtOAc, dried over $Na_2SO_4$ and this solution was filtered through a pad of silica (400 ml) and concentrated to dryness. The residue was triturated into ether:hexane 1:2, the solid filtered, washed with hexane and air dried to yield 77.3 g (77% yield) of 2.

The mother liquors were extracted with 2 N NaOH and the aqueous layer was acidified with AcOH. The precipitated solid was filtered and dried to yield a second batch of material (2.16 g, 2%).

Note: use of MeONa and/or the methyl ester of the succinate or pyridinecarboxylate will drastically decrease the speed of the reaction by lowering the boiling point of the mixture of solvents.

Step 3: Diethyl 5,8-bis(2,2,2-trifluoroethoxy)quinoline-6,7-dicarboxylate 3

A mixture containing diethyl 5,8-dihydroxyquinoline-6,7-dicarboxylate 2 (57.8 g, 189 mmol), 2,2,2-trifluoroethyl trifluoromethanesulfonate (100 g, 2.28 equiv) and $K_2CO_3$ (62.7 g, 2.4 equiv) in DMF (300 ml) was heated to 70 C for an hour. This mixture was cooled down to r.t. and added to half-saturated $NH_4Cl$ (1.5 L). After acidification with AcOH (60 ml), the product was extracted with toluene twice and once with 50% EtOAc/toluene. The combined organics were dried over $Na_2SO_4$ and filtered through a 1.2 L pad of silica to remove the polar material. The silica was washed with 10% EtOAc/toluene. Evaporation of the solvents afforded 84.68 g (95% yield) of pure product 3.

Step 4: 5,8-bis(2,2,2-Trifluoroethoxy)quinoline-6,7-dicarboxylic Acid 4

A solution containing diethyl 5,8-bis(2,2,2-trifluoroethoxy)quinoline-6,7-dicarboxylate 3 (84.7 g, 180 mmol), 5 N NaOH (180 ml), THF (360 ml) and MeOH (180 ml) was heated to 60 C for 1.5 h. This mixture was then added to half-saturated $NH_4Cl$ and acidified with 2 N HCl to pH 0-1. The product was extracted into i-PrOAc:THF 1:1, dried over $Na_2SO_4$ and concentrated. It was triturated with ether:hexane 1:4 to yield the diacid 4 as an off-white solid (approx 100% yield).

Step 5: 5,9-bis(2,2,2-Trifluoroethoxy)furo[3,4-g]quinoline-6,8-dione 5

A solution of 5,8-bis(2,2,2-trifluoroethoxy)quinoline-6,7-dicarboxylic acid 4 (180 mmol) in acetic anhydride (500 ml) was heated to reflux for 3 h and concentrated to dryness. The solid residue was triturated into 400 ml ether:hexane 1:4 to afford 68.2 g (96% yield for the last two steps) of the anhydride as a brownish solid.

Step 6: 1-{4-[6,8-Dioxo-5,9-bis(2,2,2-trifluoroethoxy)-6,8-dihydro-7H-pyrrolo[3,4-g]quinolin-7-yl]-3-methylphenyl}methanesulfonamide 6

A mixture containing 5,9-bis(2,2,2-trifluoroethoxy)furo[3,4-g]quinoline-6,8-dione (42 g, 106 mmol) 5 and 1-(4-amino-3-methylphenyl)methanesulfonamide 15 (24 g, 1.13 equiv) from Preparative Example 1 in AcOH (350 ml) was degassed under vacuum and heated to reflux under nitrogen for 6.5 h. The solvent was then evaporated and the residue was partially dissolved into 50% EtOAc/toluene (800 ml) and cooled down to 0 C. The solid was filtered and washed with toluene to yield a first crop of material as a brownish solid (50.36 g).

The mother liquors were partially concentrated until an oil starts to separate on the side of the flask. They were then filtered through a small pad of silica (450 ml) and the silica was washed with 40% EtOAc/toluene. The residue was triturated in ether containing a small amount of EtOAc to give a second crop of material (10.07 g, 99% overall yield).

Note: oxidation of the aniline to give a dimer has been observed when small amount of oxygen is present in this reaction.

Step 7: 1-{4-[8-Hydroxy-6-oxo-5,9-bis(2,2,2-trifluoroethoxy)-6,8-dihydro-7H-pyrrolo[3,4-g]quinolin-7-yl]-3-methylphenyl}methanesulfonamide 7 and 1-{4-[6-hydroxy-8-oxo-5,9-bis(2,2,2-trifluoroethoxy)-6,8-dihydro-7H-pyrrolo[3,4-g]quinolin-7-yl]-3-methylphenyl}methanesulfonamide 8

To a solution of 1-{4-[6,8-dioxo-5,9-bis(2,2,2-trifluoroethoxy)-6,8-dihydro-7H-pyrrolo[3,4-g]quinolin-7-yl]-3-methylphenyl}methanesulfonamide 6 (56.8 g, 98.3 mmol) in THF (1 L) at −20 C was added LiBH (2 M in THF, 55 ml, 1.12 equiv). The resulting solution was warmed up slowly to 5 C and stirred at that temperature o.n. to give a 2:1 mixture of 7:8. This mixture was cooled to −5 C and then added slowly into ice (2 L) and sat $NH_4Cl$ (1 L) under vigorous stirring. AcOH (30 ml) was then added portionwise, followed by i-PrOAc (1 L) and this mixture was stirred well and warmed slowly to r.t.

The products were extracted into i-PrOAc, dried over Na₂SO₄, concentrated and co-evaporated once with toluene. They were used as such in the next step.

Step 8: 1-{3-Methyl-4-[6-oxo-5,9-bis(2,2,2-trifluoroethoxy)-6,8-dihydro-7H-pyrrolo[3,4-g]quinolin-7-yl]phenyl}methanesulfonamide 9 and 1-{3-methyl-4-[8-oxo-5,9-bis(2,2,2-trifluoroethoxy)-6,8-dihydro-7H-pyrrolo[3,4-g]quinolin-7-yl]phenyl}methanesulfonamide 10

To a solution of 7 and 8 (57.8 g, 99.7 mmol) in dichloromethane (100 ml) was added triethylsilane (75 ml, 4.7 equiv) followed by trifluoroacetic acid (230 ml) and this mixture was stirred at r.t. o.n. under nitrogen. The solvents were then evaporated and the residue was dissolved into i-PrOAc:THF 1:1 (1 L) and added to an ice-cold solution of NaOAc•3H₂O (150 g) in water (1.5 L). The phases were separated and the aqueous layer reextracted twice with i-PrOAc:THF 1:1 (400 ml each time). The organics were dried over Na₂SO₄, filtered and silica gel (1.2 L) was added. After concentration, this mixture was purified by flash over silica (3 L) with EtOAc/toluene 40% to recover 9 and acetone/toluene 40% to recover its isomer 10. The major isomer 9 was triturated in ether:hexane 1:1 (300 ml) to yield 31.23 g (56% yield) of a white solid. The isomer 10 was triturated in ether:hexane 3:1 to yield 18.29 g of white solid (32% yield).

Notes: in the presence of oxygen, the hydroxylactams 7 and 8 are partially oxidized to the phthalimide 6; addition of TFA before triethylsilane affords a small amount of decomposed material.

Step 9: (1-(2,6-Dimethoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropanecarboxamide)

A mixture containing 9 (15.1 g, 26.8 mmol), 4-(dimethylamino)pyridine (6.55 g, 2 equiv), 1-(2,6-dimethoxyphenyl)cyclopropanecarboxylic acid 19 (8.85 g, 1.5 equiv) from Preparative Example 2 and EDCI (10.28 g, 2 equiv) in 1,2-dichloroethane (250 ml) was stirred at 50 C for 20 h. A saturated solution of NH₄Cl was then added and the mixture was acidified with acetic acid, extracted into dichloromethane and dried over Na₂SO₄. Flash chromatography of the residue using EtOAc:toluene:AcOH 15:85:1 gave a mixture containing Example 33 and 1-(2,6-dimethoxyphenyl)cyclopropanecarboxylic acid. Trituration twice in ether:hexane 1:1 (200 ml) yielded 17.97 g (87%) of Example 33 as a white solid.

Following the methods described herein, the compounds of Table 3 were prepared.

TABLE 3

| Example | Structure | Name | m/z |
|---|---|---|---|
| 34 | 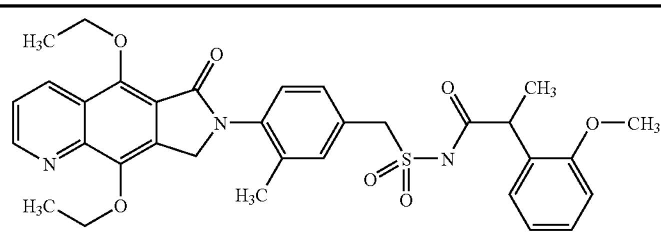 | N-{[4-(5,9-diethoxy-6-oxo-6,8-dihydro-7H-pyrrolo[3,4-g]quinolin-7-yl)-3-methylbenzyl]sulfonyl}-2-(2-methoxyphenyl)propanamide | n/a |
| 35 | 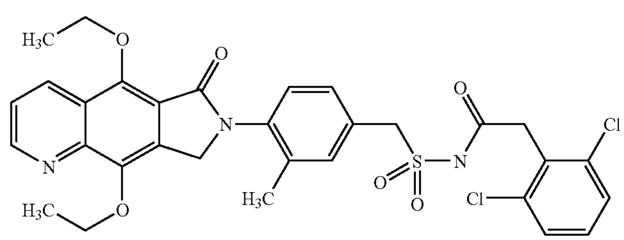 | 2-(2,6-dichlorophenyl)-N-{[4-(5,9-diethoxy-6-oxo-6,8-dihydro-7H-pyrrolo[3,4-g]quinolin-7-yl)-3-methylbenzyl]sulfonyl}acetamide | 640.0 (M − 1), 642.2 |
| 36 | 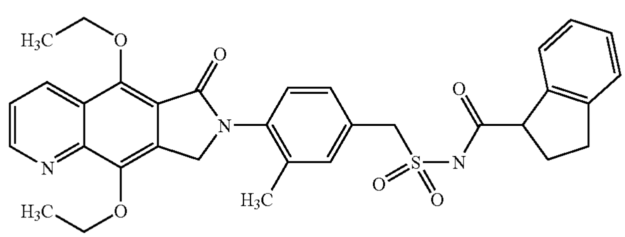 | N-{[4-(5,9-diethoxy-6-oxo-6,8-dihydro-7H-pyrrolo[3,4-g]quinolin-7-yl)-3-methylbenzyl]sulfonyl}indane-1-carboxamide | 598.3 (M − 1) |
| 37 | 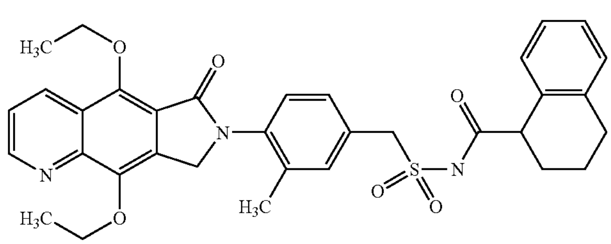 | N-{[4-(5,9-diethoxy-6-oxo-6,8-dihydro-7H-pyrrolo[3,4-g]quinolin-7-yl)-3-methylbenzyl]sulfonyl}-1,2,3,4-tetrahydronaphthalene-1-carboxamide | 612.4 (M − 1) |

TABLE 3-continued

| Example | Name | m/z |
|---|---|---|
| 38 | N-{[4-(5,9-diethoxy-6-oxo-6,8-dihydro-7H-pyrrolo[3,4-g]quinolin-7-yl)-3-methylbenzyl]sulfonyl}-2-mesitylacetamide | 614.3 (M − 1) |
| 39 | 1-(2,4-dichlorophenyl)-N-{[4-(5,9-diethoxy-6-oxo-6,8-dihydro-7H-pyrrolo[3,4-g]quinolin-7-yl)-3-methylbenzyl]sulfonyl}cyclopropane-carboxamide | 666.2 (M − 1), 668.4 |
| 40 | (2R)-N-{[4-(5,9-diethoxy-6-oxo-6,8-dihydro-7H-pyrrolo[3,4-g]quinolin-7-yl)-3-methylbenzyl]sulfonyl}-2-methoxy-2-phenylacetamide | 602.3 (M − 1) |
| 41 | (2S)-N-{[4-(5,9-diethoxy-6-oxo-6,8-dihydro-7H-pyrrolo[3,4-g]quinolin-7-yl)-3-methylbenzyl]sulfonyl}-2-methoxy-2-phenylacetamide | 602.3 (M − 1) |
| 42 | 2-(2-methoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide | 712.2 (M + 1) |
| 43 | N-({3-methyl-4-[6-oxo-5,9-bis(2,2,2-trifluoroethoxy)-6,8-dihydro-7H-pyrrolo[3,4-g]quinolin-7-yl]benzyl}sulfonyl)-2-pyridin-2-ylacetamide | 681.4 (M − 1) |

TABLE 3-continued

| Example | Structure | Name | m/z |
|---|---|---|---|
| 44 | 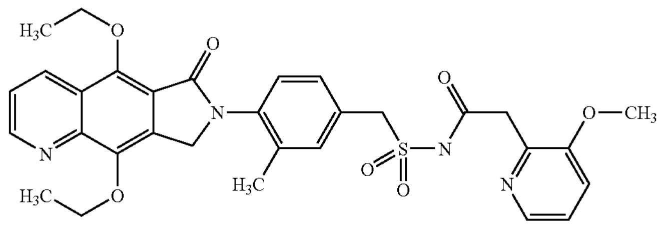 | N-{[4-(5,9-diethoxy-6-oxo-6,8-dihydro-7H-pyrrolo[3,4-g]quinolin-7-yl)-3-methylbenzyl]sulfonyl}-2-(3-methoxypyridin-2-yl)acetamide | 603.5 (M − 1) |
| 45 | 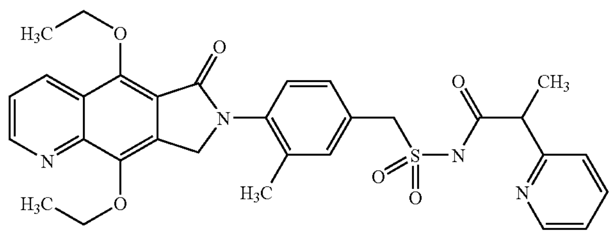 | N-{[4-(5,9-diethoxy-6-oxo-6,8-dihydro-7H-pyrrolo[3,4-g]quinolin-7-yl)-3-methylbenzyl]sulfonyl}-2-pyridin-2-ylpropanamide | 589.2 (M + 1) |
| 46 | 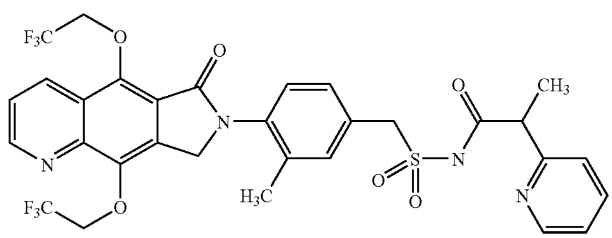 | N-({3-methyl-4-[6-oxo-5,9-bis(2,2,2-trifluoroethoxy)-6,8-dihydro-7H-pyrrolo[3,4-g]quinolin-7-yl]benzyl}sulfonyl)-2-pyridin-2-ylpropanamide | 695.2 (M − 1) |
| 47 | 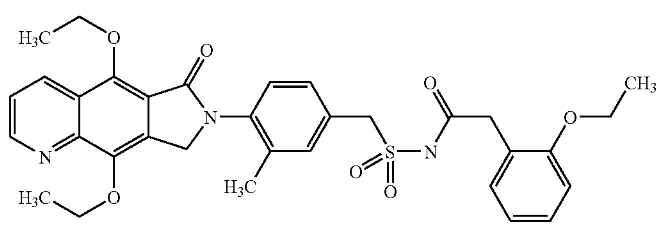 | N-{[4-(5,9-diethoxy-6-oxo-6,8-dihydro-7H-pyrrolo[3,4-g]quinolin-7-yl)-3-methylbenzyl]sulfonyl}-2-(2-ethoxyphenyl)acetamide | 616.3 (M − 1) |
| 48 | 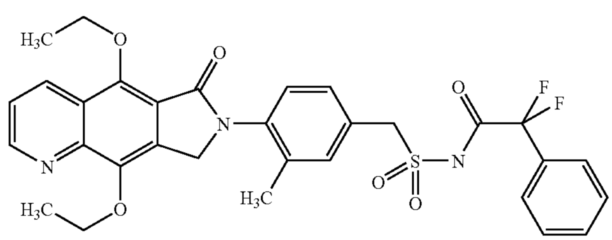 | N-{[4-(5,9-diethoxy-6-oxo-6,8-dihydro-7H-pyrrolo[3,4-g]quinolin-7-yl)-3-methylbenzyl]sulfonyl}-2,2-difluoro-2-phenylacetamide | 608.2 (M − 1) |
| 49 | 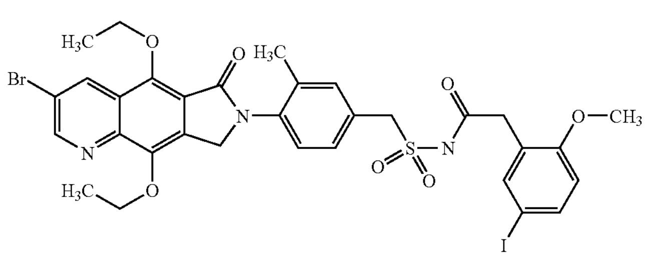 | N-{[4-(3-bromo-5,9-diethoxy-6-oxo-6,8-dihydro-7H-pyrrolo[3,4-g]quinolin-7-yl)-3-methylbenzyl]sulfonyl}-2-(5-iodo-2-methoxyphenyl)acetamide | 808.0 806.1 (M − 1) |

TABLE 3-continued

| Example | Structure | Name | m/z |
|---|---|---|---|
| 50 | 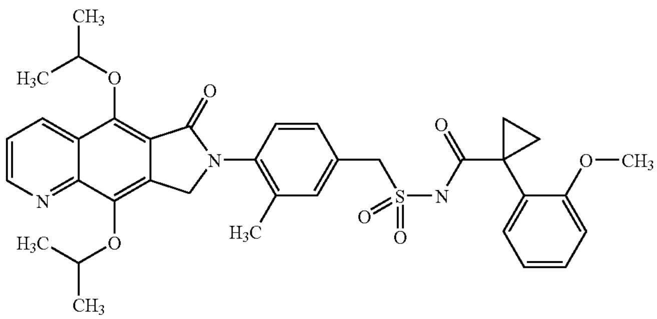 | N-{[4-(5,9-diisopropoxy-6-oxo-6,8-dihydro-7H-pyrrolo[3,4-g]quinolin-7-yl)-3-methylbenzyl]sulfonyl}-1-(2-methoxyphenyl)cyclopropanecarboxamide | 656.2 (M − 1) |
| 51 | 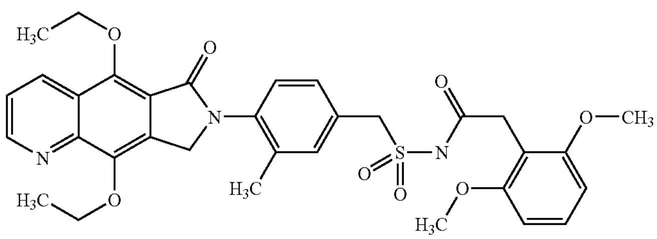 | N-{[4-(5,9-diethoxy-6-oxo-6,8-dihydro-7H-pyrrolo[3,4-g]quinolin-7-yl)-3-methylbenzyl]sulfonyl}-2-(2,6-dimethoxyphenyl)acetamide | 632.2 (M − 1) |
| 52 | 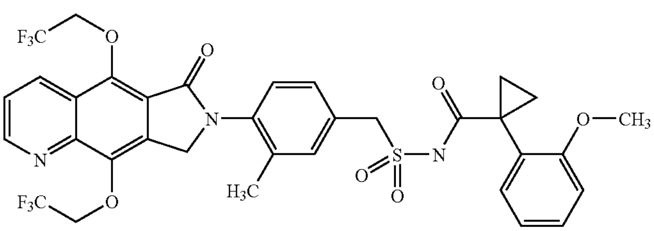 | 1-(2-methoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropanecarboxamide | 736.1 (M + 1) |
| 53 | 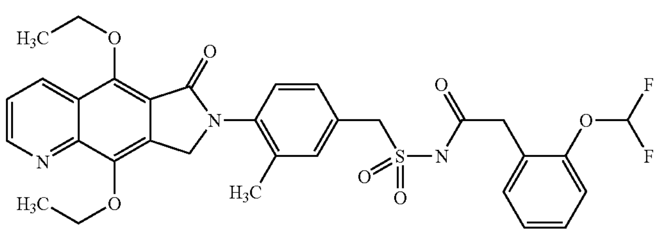 | N-{[4-(5,9-diethoxy-6-oxo-6,8-dihydro-7H-pyrrolo[3,4-g]quinolin-7-yl)-3-methylbenzyl]sulfonyl}-2-[2-(difluoromethoxy)phenyl]acetamide | 638.0 (M − 1) |
| 54 | 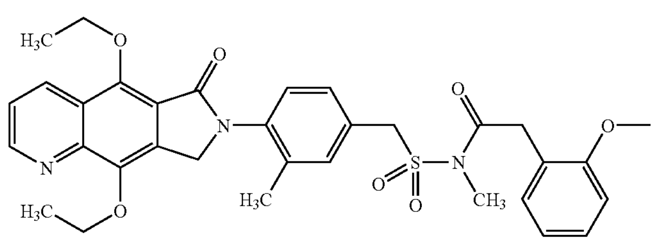 | N-{[4-(5,9-diethoxy-6-oxo-6,8-dihydro-7H-pyrrolo[3,4-g]quinolin-7-yl)-3-methylbenzyl]sulfonyl}-2-(2-methoxyphenyl)-N-methylacetamide | 618.2 (M + 1) |
| 55 | 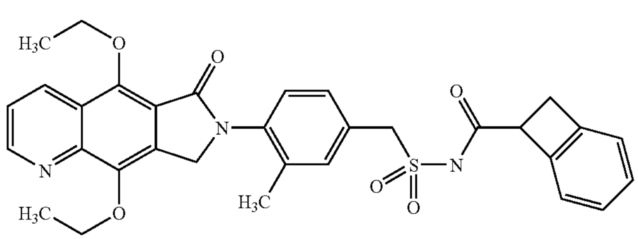 | N-{[4-(5,9-diethoxy-6-oxo-6,8-dihydro-7H-pyrrolo[3,4-g]quinolin-7-yl)-3-methylbenzyl]sulfonyl}bicyclo[4.2.0]octa-1,3,5-triene-7-carboxamide | 583.9 (M − 1) |

TABLE 3-continued

| Example | Structure | Name | m/z |
|---|---|---|---|
| 56 | 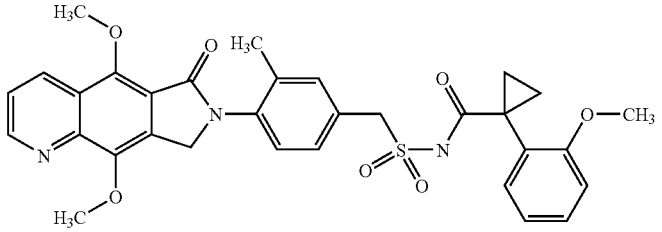 | N-{[4-(5,9-dimethoxy-6-oxo-6,8-dihydro-7H-pyrrolo[3,4-g]quinolin-7-yl)-3-methylbenzyl]sulfonyl}-1-(2-methoxyphenyl)cyclopropanecarboxamide | 599.8 (M − 1) |
| 57 | 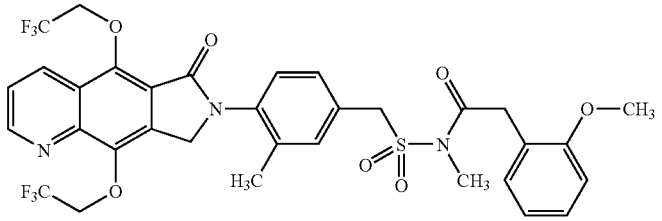 | 2-(2-methoxyphenyl)-N-methyl-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide | 726.2 (M + 1) |
| 58 | 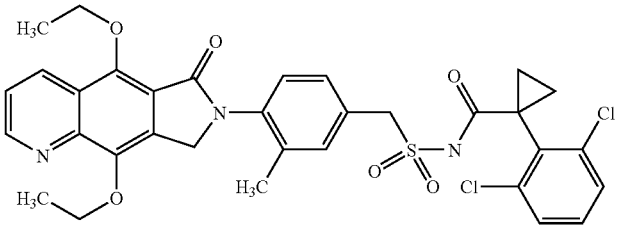 | 1-(2,6-dichlorophenyl)-N-{[4-(5,9-diethoxy-6-oxo-6,8-dihydro-7H-pyrrolo[3,4-g]quinolin-7-yl)-3-methylbenzyl]sulfonyl}cyclopropanecarboxamide | 666.2 (M − 1) |
| 59 | 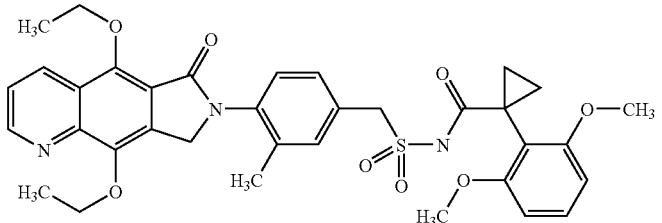 | N-{[4-(5,9-diethoxy-6-oxo-6,8-dihydro-7H-pyrrolo[3,4-g]quinolin-7-yl)-3-methylbenzyl]sulfonyl}-1-(2,6-dimethoxyphenyl)cyclopropanecarboxamide | 657.8 (M − 1) |
| 60 | 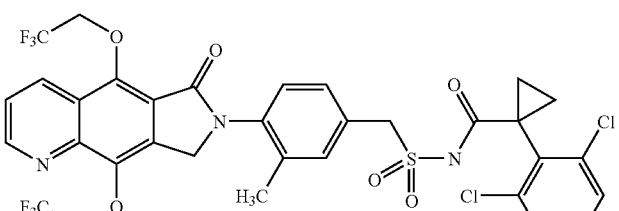 | 1-(2,6-dichlorophenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropanecarboxamide | 774.0 (M − 1), 776.0 |
| 61 | 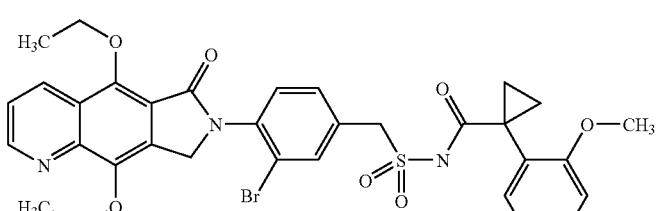 | N-{[3-bromo-4-(5,9-diethoxy-6-oxo-6,8-dihydro-7H-pyrrolo[3,4-g]quinolin-7-yl)benzyl]sulfonyl}-1-(2-methoxyphenyl)cyclopropanecarboxamide | 692.3 (M − 1), 694.3 |

TABLE 3-continued

| Example | Structure | Name | m/z |
|---|---|---|---|
| 62 | 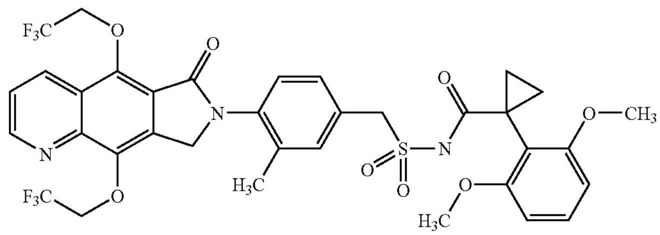 | 1-(2,6-dimethoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropane-carboxamide | 766.4 (M − 1) |
| 63 | 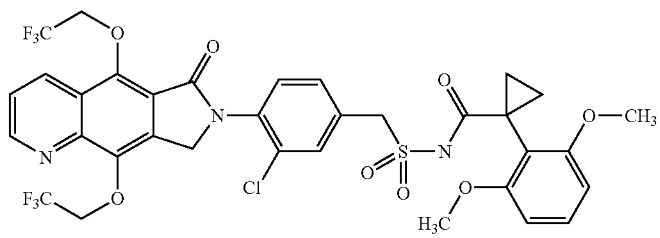 | N-({3-chloro-4-[6-oxo-5,9-bis(2,2,2-trifluoroethoxy)-6,8-dihydro-7H-pyrrolo[3,4-g]quinolin-7-yl]benzyl}sulfonyl)-1-(2,6-dimethoxyphenyl)cyclopropane-carboxamide | 787.9, 789.8 (M + 1) |
| 64 | 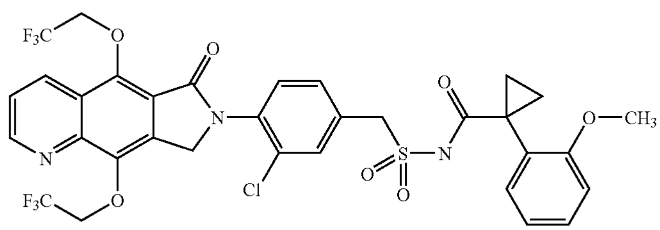 | N-({3-chloro-4-[6-oxo-5,9-bis(2,2,2-trifluoroethoxy)-6,8-dihydro-7H-pyrrolo[3,4-g]quinolin-7-yl]benzyl}sulfonyl)-1-(2-methoxyphenyl)cyclopropanecarbox-amide | 757.8, 760.0 (M + 1) |
| 65 | 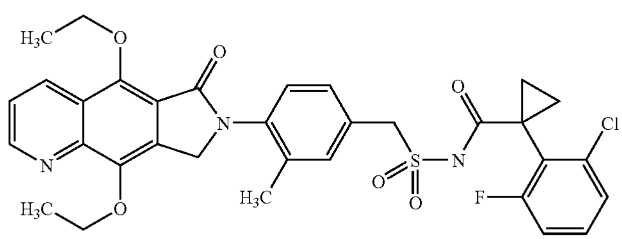 | 1-(2-chloro-6-fluorophenyl)-N-{[4-(5,9-diethoxy-6-oxo-6,8-dihydro-7H-pyrrolo[3,4-g]quinolin-7-yl)-3-methylbenzyl]sulfonyl}cyclopropane-carboxamide | 650.2 (M − 1) |
| 66 | 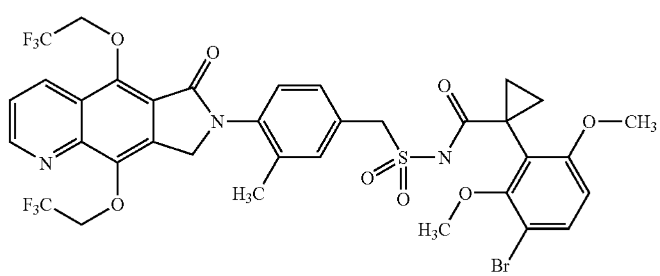 | 1-(3-bromo-2,6-dimethoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropane-carboxamide | 844.1 (M − 1) |
| 67 | 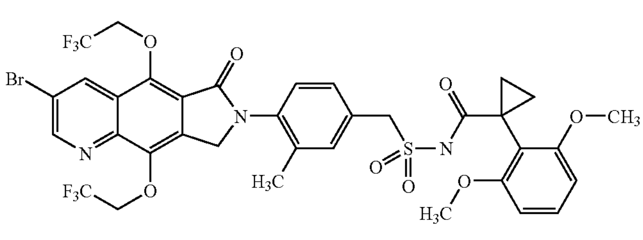 | N-({4-[3-bromo-6-oxo-5,9-bis(2,2,2-trifluoroethoxy)-6,8-dihydro-7H-pyrrolo[3,4-g]quinolin-7-yl]-3-methylbenzyl}sulfonyl)-1-(2,6-dimethoxyphenyl)cyclopropane-carboxamide | n/a |

TABLE 3-continued

| Example | Structure | Name | m/z |
|---|---|---|---|
| 68 | 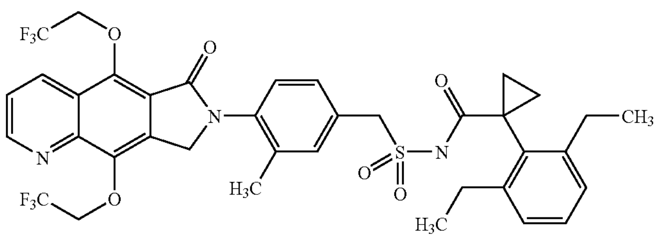 | 1-(2,6-diethylphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropanecarboxamide | 764.0 (M + 1) |
| 69 | 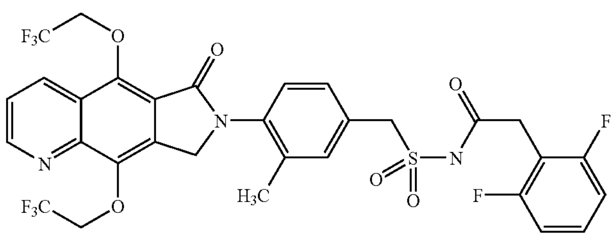 | 2-(2,6-difluorophenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide | 715.9 (M − 1) |
| 70 | 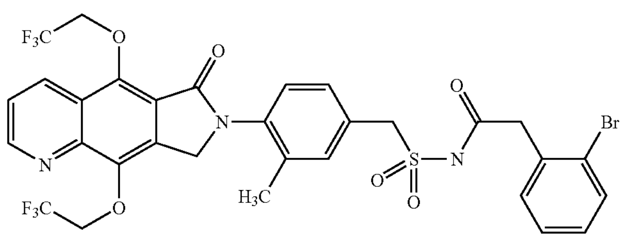 | 2-(2-bromophenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide | 758.0 (M − 1), 760.0 |
| 71 | 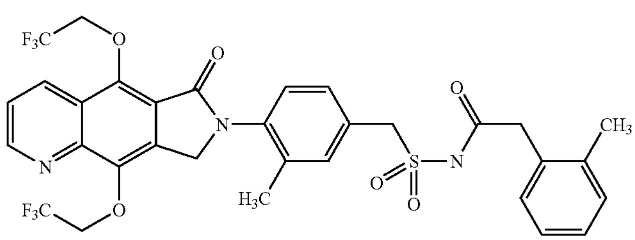 | N-({3-methyl-4-[6-oxo-5,9-bis(2,2,2-trifluoroethoxy)-6,8-dihydro-7H-pyrrolo[3,4-g]quinolin-7-yl]benzyl}sulfonyl)-2-(2-methylphenyl)acetamide | 694.0 (M − 1) |
| 72 | 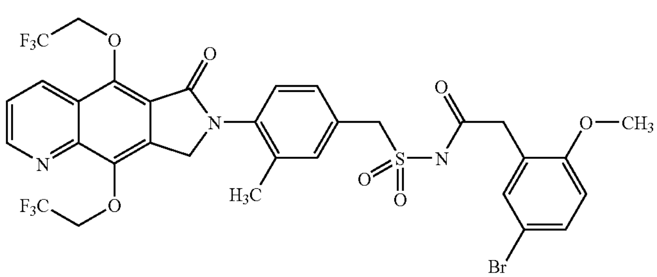 | 2-(5-bromo-2-methoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide | 788.0 (M − 1), 789.9 |
| 73 | 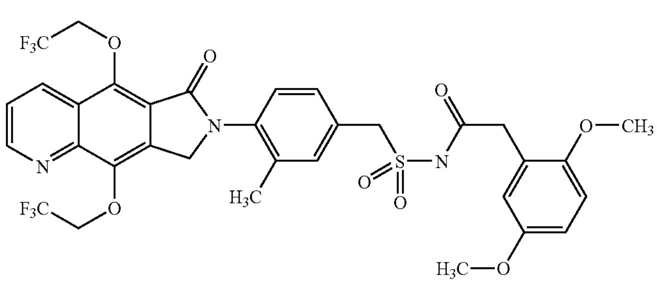 | 2-(2,5-dimethoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide | 740.0 (M − 1) |

TABLE 3-continued

| Example | Structure | Name | m/z |
|---|---|---|---|
| 74 | 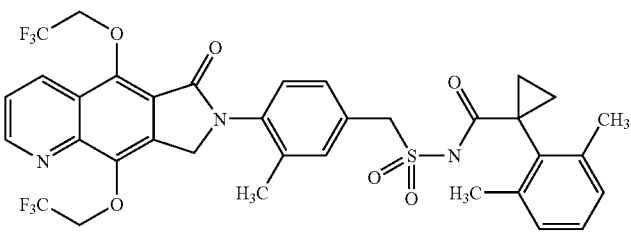 | 1-(2,6-dimethylphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropane-carboxamide | 733.9 (M − 1) |
| 75 | 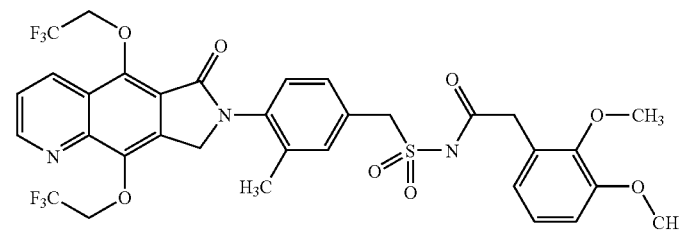 | 2-(2,3-dimethoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide | 740.0 (M − 1) |
| 76 | 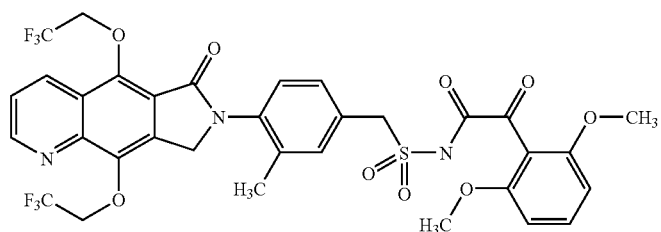 | 2-(2,6-dimethoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)-2-oxoacetamide | 754.0 (M − 1) |
| 77 | 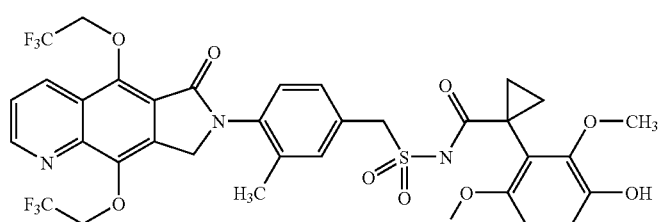 | 1-(3-hydroxy-2,6-dimethoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclo-propane-carboxamide | 782.8 (M − 1) |
| 78 | 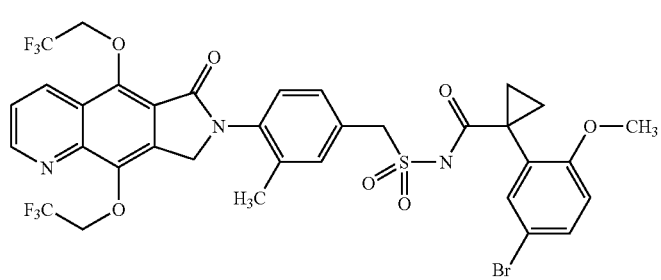 | 1-(5-bromo-2-methoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropane-carboxamide | 814.2 (M − 1), 816.2 |
| 79 | 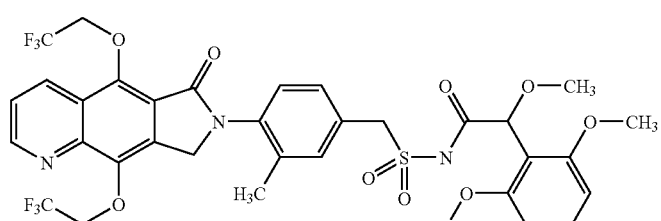 | 2-(2,6-dimethoxyphenyl)-2-methoxy-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide | 770.1 (M − 1) |

TABLE 3-continued

| Example | Structure | Name | m/z |
|---|---|---|---|
| 80 | 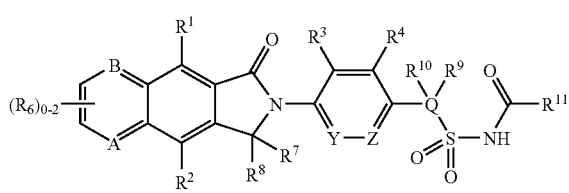 | 2-(2,3-dichlorophenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide | 748.0 (M − 1), 750.1 |

In another embodiment, the invention encompasses a compound according of Formula I

I or a pharmaceutically acceptable salt thereof, wherein:

A is selected from the group consisting of N or CH,

B is selected from the group consisting of N or CH, with the proviso that A and B cannot both simultaneously be CH;

Y and Z are independently selected from the group consisting of: N, N(O) and $C(R^5)$;

Q is N or C;

$R^1$ to $R^6$ are independently selected from the group consisting of: H, halogen, $C_{1-6}$alkyl, $C_{3-6}$cycloalkyl, $C_{1-6}$fluoroalkyl, $C_{1-6}$alkoxy, $C_{1-6}$fluoroalkoxy, $C_{3-6}$cycloalkoxy, $C_{3-6}$cycloalkylmethoxy, $NH_2$, —$NHC_{1-4}$alkyl, —$N(C_{1-4}$alkyl$)_2$, $NO_2$, OH and CN;

$R^7$ and $R^8$ are independently selected from the group consisting of: H and $C_{1-6}$alkyl or $R^7$ and $R^8$ can join to make a carbonyl or 3-6 membered monocyclic cycloalkane ring;

$R^9$ and $R^{10}$ are selected from the group consisting of: H and $C_{1-6}$alkyl or $R^9$ and $R^{10}$ can join to make a 3-6 membered monocyclic cycloalkane ring, with the proviso that $R^9$ is not present when Q is N;

$R^{11}$ is selected from the group consisting of: (a) $C_{1-6}$alkyl, (b) $C_{3-6}$cycloalkyl, (c) $C_{3-6}$cycloalkyl substituted by one to three substituents independently selected from $R^{12}$; (d) aryl, (e) aryl substituted by one to three substituents independently selected from $R^{12}$, (f) heteroaryl, (g) heteroaryl substituted by one to three substituents independently selected from $R^{12}$, (h) heterocyclyl, (i) heterocyclyl substituted by one to three substituents independently selected from $R^{12}$, (j) —$C_{1-6}$alkylaryl, (k) —$C_{1-6}$alkylaryl substituted by one to five substituents independently selected from $R^{12}$, (k) —$C_{1-6}$alkyl-$C_{3-6}$cycloalkyl; (l) —$C_{1-6}$alkyl-$C_{3-6}$cycloalkyl substituted by one to five substituents independently selected from $R^{12}$; (m) —$C_{1-6}$alkylheteroaryl; (n) —$C_{1-6}$alkylheteroaryl substituted by one to five substituents independently selected from $R^{12}$; (o)—$C_{1-6}$alkylheterocyclyl; and (p) —$C_{1-6}$alkylheterocyclyl substituted by one to five substituents independently selected from $R^{12}$; and fused analogs of (b) to (p); and $R^{12}$ is selected from the group consisting of: halogen, $C_{1-6}$alkyl, $C_{1-6}$fluoroalkyl, $C_{3-6}$cycloalkyl, $C_{1-6}$alkoxy, $C_{1-6}$fluoroalkoxy, $C_{3-6}$cycloalkoxy, $NH_2$, —$NHC_{1-4}$alkyl or —$N(C_{1-4}$alkyl$)_2$, $NO_2$ and OH, or two $R^{12}$ groups attached to the same atom may be joined together to form a spiro $C_{3-6}$cycloalkyl group.

For purposes of this specification, for the terms "—$C_{1-6}$alkylaryl substituted by one to five substituents independently selected from $R^{12}$", "—$C_{1-6}$alkyl-$C_{3-6}$cycloalkyl substituted by one to five substituents independently selected from $R^{12}$", "—$C_{1-6}$alkylheteroaryl substituted by one to five substituents independently selected from $R^{12}$" and "—$C_{1-16}$alkylheterocyclyl substituted by one to five substituents independently selected from $R^{12}$" as well as the corresponding terms having one to three substituents, the substituent $R^{12}$ may be substituted on any substitutable position, i.e., on the alkyl portion or the aryl, $C_{3-6}$cycloalkyl, heteroaryl or heterocyclyl portion.

In another embodiment, the invention encompasses a compound according of Formula Ib Ib

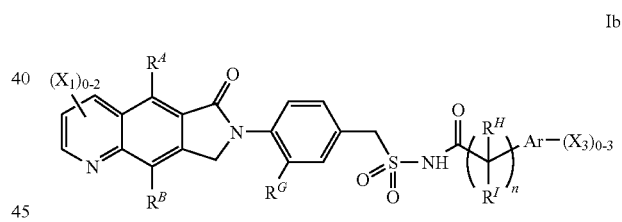

or a pharmaceutically acceptable salt thereof, wherein:

n is 0 or 1;

Ar is selected from the group consisting of: $C_{3-6}$cycloalkyl, aryl, heteroaryl and heterocyclyl, or a fused analog of $C_{3-6}$cycloalkyl, aryl, heteroaryl and heterocyclyl;

$R^A$ and $R^B$ are the same and selected from the group consisting of: ethoxy, 2,2,2-trifluoroethoxy and isopropoxy;

$R^G$ is selected from the group consisting of: Cl, Br and methyl;

$R^H$ and $R^I$ are independently selected from the group consisting of: hydrogen, halogen, methyl and methoxy; or $R^H$ and $R^I$ may be joined together to form a cyclopropyl ring; and each $X_1$, $X_2$ and $X_3$ is independently selected from the group consisting of: halogen, $C_{1-4}$alkyl, $C_{1-4}$fluoroalkyl, $C_{1-4}$alkoxy, $C_{1-4}$fluoroalkoxy and OH.

Within this embodiment, the invention encompasses a compound of Formula Ib wherein:

$X_1$ is not present;

$R^A$ and $R^B$ are both 2,2,2-trifluoroethoxy; and $R^G$ is methyl.

Also within this embodiment, the invention encompasses a compound of Formula Ib wherein:
$X_1$ is not present;
$R^A$ and $R^B$ are both 2,2,2-trifluoroethoxy;
$R^G$ is methyl;
n is 1; and
$R^H$ and $R^I$ are be joined together to form a $_{3-6}$cycloalkyl ring.

Also within this embodiment, the invention encompasses a compound of Formula Ib wherein:
$X_1$ is not present;
$R^A$ and $R^B$ are both 2,2,2-trifluoroethoxy;
$R^G$ is methyl;
n is 1;
$R^H$ and $R^I$ are be joined together to form a $_{3-6}$cycloalkyl ring; and
Ar is phenyl.

The invention also encompasses a compound of Formula Ia

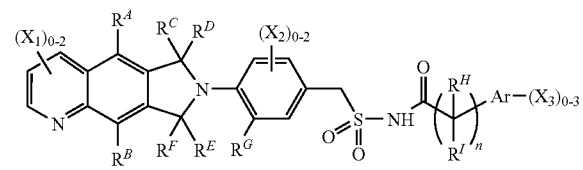

Ia or a pharmaceutically acceptable salt thereof, wherein:
n is 0 or 1;
Ar is selected from the group consisting of: $C_{3-6}$cycloalkyl, aryl, heteroaryl and heterocyclyl, or a fused analog of $C_{3-6}$cycloalkyl, aryl, heteroaryl and heterocyclyl;
$R^A$ and $R^B$ are independently selected from the group consisting of $C_{1-4}$alkyl, $C_{1-4}$fluoroalkyl, $C_{1-4}$alkoxy, $C_{1-4}$fluoroalkoxy, $C_{3-6}$cycloalkyl, $C_{3-6}$cycloalkoxy and $C_{3-6}$cycloalkylmethoxy;
$R^C$ and $R^D$ or $R^E$ and $R^F$ or both are joined together to form carbonyl, and otherwise are hydrogen;
$R^G$ is selected from the group consisting of: F, Cl, Br, I, methyl, ethyl, methoxy, $CF_3$, $CF_3O$— and CN;
$R^H$ and $R^I$ are independently hydrogen or methyl; or $R^H$ and $R^I$ may be joined together to form a $C_{3-6}$cycloalkyl ring; and
each $X_1$, $X_2$ and $X_3$ is independently selected from the group consisting of: F, Cl, Br, I, methyl, ethyl, methoxy, $CF_3$, $CF_3O$— and OH.

Within this embodiment, the invention encompasses a compound of Formula Ia wherein $R^A$ and $R^B$ are $CF_2HO$—.

The term "fluoroalkyl" means alkyl as defined above wherein one or more of the hydrogen atoms have been replaced by fluoro atoms. The term "fluoroalkoxy" means alkoxy as defined above wherein one or more of the hydrogen atoms have been replaced by fluoro atoms.

The compounds of the invention are also useful for treating or preventing a neoplasia in a subject in need of such treatment or prevention. The term "treatment" includes partial or total inhibition of the neoplasia growth, spreading or metastasis, as well as partial or total destruction of the neoplastic cells. The term "prevention" includes either preventing the onset of clinically evident neoplasia altogether or preventing the onset of a preclinically evident stage of neoplasia in individuals at risk. Also intended to be encompassed by this definition is the prevention of initiation for malignant cells or to arrest or reverse the progression of premalignant cells to malignant cells. This includes prophylactic treatment of those at risk of developing the neoplasia. The term "subject" for purposes of treatment includes any human or mammal subject who has any one of the known neoplasias, and preferably is a human subject. For methods of prevention, the subject is any human or animal subject, and preferably is a human subject who is at risk for obtaining a neoplasia. The subject may be at risk due to exposure to carcinogenic agents, being genetically predisposed to have the neoplasia, and the like.

The term "neoplasia" includes both benign and cancerous tumors, growths and polyps. Thus, the compounds of the invention are useful for treating or preventing benign tumors, growths and polyps including squamous cell papilloma, basal cell tumor, transitional cell papilloma, adenoma, gastrinoma, cholangiocellular adenoma, hepatocellular adenoma, renal tubular adenoma, oncocytoma, glomus tumor, melanocytic nevus, fibroma, myxoma, lipoma, leiomyoma, rhabdomyoma, benign teratoma, hemangioma, osteoma, chondroma and meningioma. The compounds of the invention are also useful for treating or preventing cancerous tumors, growths and polyps including squamous cell carcinoma, basal cell carcinoma, transitional cell carcinoma, adenocarcinoma, malignant gastrinoma, cholangiocelleular carcinoma, hepatocellular carcinoma, renal cell carcinoma, malignant melanoma, fibrosarcoma, myxosarcoma, liposarcoma, leimyosarcoma, rhabdomyosarcoma, malignant teratoma, hemangiosarcoma, Kaposi sarcoma, lymphangiosarcoma, ostreosarcoma, chondrosarcoma, malignant meningioma, non-Hodgkin lymphoma, Hodgkin lymphoma and leukemia. For purposes of this specification, "neoplasia" includes brain cancer, bone cancer, epithelial cell-derived neoplasia (epithelial carcinoma), basal cell carcinoma, adenocarcinoma, gastrointestinal cancer such as lip cancer, mouth cancer, esophogeal cancer, small bowel cancer and stomach cancer, colon cancer, rectal cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that affect epithelial, mesenchymal or blood cells throughout the body. The compounds of the invention are useful for treating or preventing any of the aforementioned cancers. The compounds of the invention are useful for treating or preventing benign and cancerous tumors, growths and polyps of the following cell types: squamous epithelium, basal cells, transitional epithelium, glandular epithelium, G cells, bile ducts epithelium, hepatocytes, tubules epithelium, melanocytes, fibrous connective tissue, cardiac skeleton, adipose tissue, smooth muscle, skeletal muscle, germ cells, blood vessels, lymphatic vessels, bone, cartilage, meninges, lymphoid cells and hematopoietic cells. The compounds can be used to treat subjects having adenomatous polyps, including those with familial adenomatous polyposis (FAP). Additionally, the compounds can be used to prevent polyps from forming in patients at risk of FAP. Preferably, the compounds of the invention are useful for treating or preventing the following cancers: colorectal, esophagus stomach, breast, head and neck, skin, lung, liver, gall bladder, pancreas, bladder, endometrium cervix, prostate, thyroid and brain.

What is claimed is:
1. A compound according to the following formula:

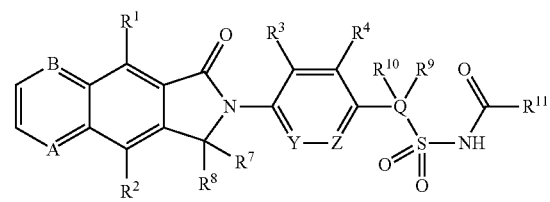

or a pharmaceutically acceptable salt thereof, wherein:
A is N,
B is CH;
Y and Z are CH;
Q is C;

R¹ and R² are independently selected from the group consisting of: $C_{1-6}$alkoxy, $C_{1-6}$fluoroalkoxy, $C_{3-6}$cycloalkoxy, $C_{3-6}$cycloalkylmethoxy, and $C_{1-6}$perfluoroalkoxy;

R³ and R⁴ are independently selected from the group consisting of: H, halogen, $C_{1-6}$alkyl, $C_{3-6}$cycloalkyl, $C_{1-6}$fluoroalkyl, $C_{1-6}$alkoxy, $C_{1-6}$fluoroalkoxy, $C_{3-6}$cycloalkoxy, $C_{3-6}$cycloalkylmethoxy, $NH_2$, —$NHC_{1-4}$alkyl, —$N(C_{1-4}alkyl)_2$, $NO_2$, OH and CN;

R⁷ to R¹⁰ are H;

R¹¹ is selected from the group consisting of: (a) $C_{1-6}$alkyl, (b) $C_{3-6}$cycloalkyl, (c) $C_{3-6}$cycloalkyl substituted by one to three substituents independently selected from R¹²; (d) aryl, (e) aryl substituted by one to three substituents independently selected from R¹², (f) heteroaryl, (g) heteroaryl substituted by one to three substituents independently selected from R¹², (h) heterocyclyl, (i) heterocyclyl substituted by one to three substituents independently selected from R¹², (j) —$C_{1-6}$alkylaryl, (k) —$C_{1-6}$alkylaryl substituted by one to five substituents independently selected from R¹², (k) —$C_{1-6}$alkyl-$C_{3-6}$cycloalkyl; (l) —$C_{1-6}$alkyl-$C_{3-6}$cycloalkyl substituted by one to five substituents independently selected from R¹²; (m) —$C_{1-6}$alkylhetereoaryl; (n) —$C_{1-6}$alkylheteroaryl substituted by one to five substituents independently selected from R¹²; (o) —$C_{1-6}$alkylheterocyclyl; and (p) —$C_{1-6}$alkylheterocyclyl substituted by one to five substituents independently selected from R¹²; and fused analogs of (b) to (p); and R¹² is selected from the group consisting of: halogen, $C_{1-6}$alkyl, $C_{1-6}$fluoroalkyl, $C_{3-6}$cycloalkyl, $C_{1-6}$alkoxy, $C_{1-6}$fluoroalkoxy, $C_{3-6}$cycloalkoxy, NH2, —$NHC_{1-4}$alkyl or —$N(C_{1-4}alkyl)_2$, $NO_2$ and OH, or two R¹² groups attached to the same atom may be joined together to form a Spiro $C_{3-6}$cycloalkyl group.

2. A compound according to claim 1 or a pharmaceutically acceptable salt thereof, wherein:

R¹¹ is selected from the group consisting of: (a) —$C_{1-6}$alkylaryl substituted by one to three substituents independently selected from R¹², (b) —$C_{1-6}$alkyl-$C_{3-6}$cycloalkyl substituted by one to three substituents independently selected from R¹²; (c) —$C_{1-6}$alkylheteroaryl substituted by one to three substituents independently selected from R¹²; and (d) —$C_{1-6}$alkylheterocyclyl substituted by one to three substituents independently selected from R¹²; and fused analogs of (b) to (d); and R¹² is selected from the group consisting of: halogen, $C_{1-6}$alkyl, $C_{1-6}$perfluoroalkyl, $C_{3-6}$cycloalkyl, $C_{1-6}$alkoxy, $C_{1-6}$perfluoroalkoxy, $C_{3-6}$cycloalkoxy, NH2, —$NHC_{1-4}$alkyl or —$N(C_{1-4}alkyl)_2$, $NO_2$ and OH.

3. The compound according to claim 2 wherein R³ is other than H.

4. The compound according to claim 1 having the following formula:

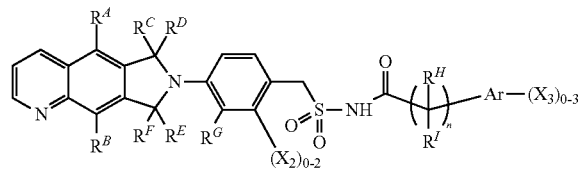

or a pharmaceutically acceptable salt thereof, wherein:
n is 0 or 1;
Ar is selected from the group consisting of: $C_{3-6}$cycloalkyl, aryl, heteroaryl and heterocyclyl, or a fused analog of $C_{3-6}$cycloalkyl, aryl, heteroaryl and heterocyclyl;

R^A and R^B are independently selected from the group consisting of $C_{1-4}$alkoxy, $C_{1-4}$perfluoroalkoxy, $C_{3-6}$cycloalkoxy and $C_{3-6}$cycloalkylmethoxy;

R^C and R^D are joined together to form carbonyl and R^E and R^F are hydrogen;

R^G is selected from the group consisting of: F, Cl, Br, I, methyl, ethyl, methoxy, $CF_3$, $CF_3O$— and CN;

R^H and R^I are independently hydrogen or methyl; or R^H and R^I may be joined together to form a $C_{3-6}$cycloalkyl ring; and each $X_2$ and $X_3$ is independently selected from the group consisting of: F, Cl, Br, I, methyl, ethyl, methoxy, $CF_3$, $CF_3O$— and OH.

5. The compound according to claim 4 wherein n is 1 and Ar is selected from the group consisting of phenyl, naphthyl and pyridyl; or n is 0 and Ar is selected from the group consisting of: indanyl and tetrahydronaphthyl.

6. The compound according to claim 5 wherein n is 1 and Ar is phenyl.

7. The compound according to claim 6 wherein at least one $X_3$ is present and is attached at the 2-position on the phenyl ring.

8. The compound according to claim 6 wherein $X_3$ is methoxy.

9. The compound according to claim 1 selected from the group consisting of:

(1) N-{[4-(5,9-diethoxy-6-oxo-6,8-dihydro-7H -pyrrolo[3,4-g]quinolin-7-yl)-3-methylbenzyl]sulfonyl}-2-(2-methoxyphenyl)acetamide;

(2) N-{[4-(5,9-diethoxy-6-oxo-6,8-dihydro-7H -pyrrolo[3,4-g]quinolin-7-yl)benzyl]sulfonyl}-2-phenylacetamide;

(3) N-{[4-(5,9-diethoxy-6-oxo-6,8-dihydro-7H -pyrrolo[3,4-g]quinolin-7-yl)-3-methylbenzyl]sulfonyl}-2-phenylacetamide;

(4) N-{[4-(5,9-diethoxy-6-oxo-6,8-dihydro-7H -pyrrolo[3,4-g]quinolin-7-yl)-3-methylbenzyl]sulfonyl}-2-phenylpropanamide;

(5) N-{[4-(5,9-diethoxy-6-oxo-6,8-dihydro-7H -pyrrolo[3,4-g]quinolin-7-yl)-3-methylbenzyl]sulfonyl }-2[2-(trifluoromethyl)phenyl]acetamide;

(6) N-{[4-(5,9-diethoxy-6-oxo-6,8-dihydro-7H -pyrrolo[3,4-g]quinolin-7-yl)-3-methylbenzyl]sulfonyl}-2-(2-fluorophenyl)acetamide;

(7) N-{[4-(5,9-diethoxy-6-oxo-6,8-dihydro-7H -pyrrolo[3,4-g]quinolin-7-yl)-3-methylbenzyl]sulfonyl}-2-pyridin-4-ylacetamide;

(8) N-{[4-(5,9-diethoxy-6-oxo-6,8-dihydro-7H -pyrrolo[3,4-g]quinolin-7-yl)-3-methylbenzyl]sulfonyl}-2-pyridin-3-ylacetamide;

(9) N-{[4-(5,9-diethoxy-6-oxo-6,8-dihydro-7H -pyrrolo[3,4-g]quinolin-7-yl)-3 -methylbenzyl]sulfonyl}-2-pyridin-2-ylacetamide;

(10) 2-(2-chlorophenyl)-N-{[4-(5,9-diethoxy-6-oxo-6,8-dihydro-7H-pyrrolo[3,4-g]quinolin-7-yl)-3-methylbenzyl]sulfonyl}acetamide;

(11) N-{[4-(5,9-diethoxy-6-oxo-6,8-dihydro-7H -pyrrolo[3,4-g]quinolin-7-yl)-3-methylbenzyl]sulfonyl}-1-phenylcyclopropanecarboxamide;

(12) N-{[4-(5,9-diethoxy-6-oxo-6,8-dihydro-7H -pyrrolo[3,4-g]quinolin-7-yl)-3 -methylbenzyl]sulfonyl}-[2-(trifluoromethoxy)phenyl]acetamide;

(13) N-{[4-(5,9-diethoxy-6-oxo-6,8-dihydro-7H -pyrrolo[3,4-g]quinolin-7-yl)-3-methylbenzyl]sulfonyl}-2-(2,5-dimethoxyphenyl)acetamide;

(14) 2-(5-bromo-2-methoxyphenyl)-N-{[4-(5,9-diethoxy-6-oxo-6,8-dihydro-7H -pyrrolo[3,4-g]quinolin-7-yl)-3-methylbenzyl]sulfonyl}acetamide;

(15) N-{[4-(5,9-diethoxy-6-oxo-6,8-dihydro-7H-pyrrolo[3,4-g]quinolin-7-yl)-3-methylbenzyl]sulfonyl}-2-(1-naphthyl)acetamide;
(16) N-{[4-(5,9-diethoxy-8-oxo-6,8-dihydro-7H-pyrrolo[3,4-g]quinolin-7-yl)benzyl]sulfonyl}-2-phenylacetamide;
(17) N-{[4-(5,9-diethoxy-8-oxo-6,8-dihydro-7H-pyrrolo[3,4-g]quinolin-7-yl)-3-methylbenzyl]sulfonyl}-2-phenylacetamide;
(18) N-{[4-(5,9-diethoxy-6-oxo-6,8-dihydro-7H-pyrrolo[3,4-g]quinolin-7-yl)-3-methylbenzyl]sulfonyl}-1-(2-methoxyphenyl)cyclopropanecarboxamide;
(19) N-{[4-(5,9-diisopropoxy-6-oxo-6,8-dihydro-7H-pyrrolo[3,4-g]quinolin-7-yl)-3-methylbenzyl]sulfonyl}-2-(2-methoxyphenyl)acetamide;
(20) 2-(2-methoxyphenyl)-N-({3-methyl-4[6-oxo-5,9-bis(2,2,2-trifluoroethoxy)-6,8-dihydro-7H-pyrrolo[3,4-g]quinolin-7-yl]benzyl}sulfonyl)propanamide;
(21) N-({4-[5,9-bis(cyclopropyloxy)-6-oxo-6,8-dihydro-7H-pyrrolo[3,4-g]quinolin-7-yl]-3-methylbenzyl}sulfonyl)-2-(2-methoxyphenyl)acetamide;
(22) N-{[3-bromo-4-(5,9-diethoxy-6-oxo-6,8-dihydro-7H-pyrrolo[3,4-g]quinolin-7-yl)benzyl]sulfonyl}-2-methyl-2-(1-naphthyl)propanamide;
(23) N-{[4-(5-ethoxy-9-isopropoxy-6-oxo-6,8-dihydro-7H-pyrrolo[3,4-g]quinolin-7-yl)-3-methylbenzyl]sulfonyl}-2-pyridin-2-ylpropanamide;
(24) N-({3-methyl-4-[6-oxo-5,9-bis(trifluoromethoxy)-6,8-dihydro-7H-pyrrolo[3,4-g]quinolin-7-yl]benzyl}sulfonyl)-2-pyridin-2-ylacetamide; and
(25) N-({4-[5,9-bis(difluoromethoxy)-6-oxo-6,8-dihydro-7H-pyrrolo[3,4-g]quinolin-7-yl]-3-methylbenzyl}sulfonyl)-2-(2-chloro-5-fluorophenyl)-2-methylpropanamide;
or a pharmaceutically acceptable salt of any of the above.

10. A pharmaceutical composition comprising a compound according to claim 1 in admixture with one or more physiologically acceptable carriers or excipients.

11. A compound according to claim 1 having the following formula:

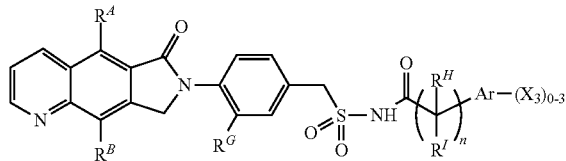

or a pharmaceutically acceptable salt thereof, wherein:
n is 0 or 1;
Ar is selected from the group consisting of: $C_{3-6}$cycloalkyl, aryl, heteroaryl and heterocyclyl, or a fused analog of $C_{3-6}$cycloalkyl, aryl, heteroaryl and heterocyclyl;
$R^A$ and $R^B$ are the same and selected from the group consisting of: ethoxy, 2,2,2-trifluoroethoxy and isopropoxy;
$R^G$ is selected from the group consisting of: Cl, Br and methyl;
$R^H$ and $R^I$ are independently selected from the group consisting of: hydrogen, halogen, methyl and methoxy; or $R^H$ and $R^I$ may be joined together to form a cyclopropyl ring; and
$X_3$ is selected from the group consisting of: halogen, $C_{1-4}$alkyl; $C_{1-4}$fluoroalkyl, $C_{1-4}$alkoxy, $C_{1-4}$fluoroalkoxy and OH.

12. The compound according to claim 11, wherein:
$R^A$ and $R^B$ are both 2,2,2-trifluoroethoxy; and
$R^G$ is methyl.

13. The compound according to claim 12, wherein:
n is 1; and
$R^H$ and $R^I$ are joined together to form a cyclopropyl ring.

14. The compound according to claim 13 wherein Ar is phenyl.

15. A compound according to claim 1 selected from the following group:
(1) N-{[4-(5,9-diethoxy-6-oxo-6,8-dihydro-7H-pyrrolo[3,4-g]quinolin-7-yl)-3-methylbenzyl]sulfonyl}-2-(2-methoxyphenyl)propanamide;
(2) 2-(2,6-dichlorophenyl)-N-{[4-(5,9-diethoxy-6-oxo-6,8-dihydro-7H-pyrrolo[3,4-g]quinolin-7-yl)-3-methylbenzyl]sulfonyl}acetamide;
(3) N-{[4-(5,9-diethoxy-6-oxo-6,8-dihydro-7H-pyrrolo[3,4-g]quinolin-7-yl)-3-methylbenzyl]sulfonyl}indane-1-carboxamide;
(4) N-{[4-(5,9-diethoxy-6-oxo-6,8-dihydro-7H-pyrrolo[3,4-g]quinolin-7-yl)-3-methylbenzyl]sulfonyl}-1,2,3,4-tetrahydronaphthalene-1-carboxamide;
(5) N-{[4-(5,9-diethoxy-6-oxo-6,8-dihydro-7H-pyrrolo[3,4-g]quinolin-7-yl)-3-methylbenzyl]sulfonyl}-2-mesitylacetamide;
(6) 1-(2,4-dichlorophenyl)-N-{[4-(5,9-diethoxy-6-oxo-6,8-dihydro-7H-pyrrolo[3,4-]quinolin-7-yl1)-3-methylbenzyl]sulfonyl}cyclopropanecarboxamide;
(7) (2R)-N-{[4-(5,9-diethoxy-6-oxo-6,8-dihydro-7H-pyrrolo[3,4-g]quinolin-7-yl)-3-methylbenzyl]sulfonyl}-2-methoxy-2-phenylacetamide;
(8) (2S)-N-{[4-(5,9-diethoxy-6-oxo-6,8-dihydro-7H-pyrrolo[3,4-g]quinolin-7-yl)-3-methylbenzyl]sulfonyl}-2-methoxy-2-phenylacetamide;
(9) 2-(2-methoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide;
(10) N-({3-methyl-4-[6-oxo-5,9-bis(2,2,2-trifluoroethoxy)-6,8-dihydro-7H-pyrrolo[3,4-g]quinolin-7-yl]benzyl}sulfonyl)-2-pyridin-2-ylacetamide;
(11) N-{[4-(5,9-diethoxy-6-oxo-6,8-dihydro-7H-pyrrolo[3,4-g]quinolin-7-yl)-3-methylbenzyl]sulfonyl}-2-(3-methoxypyridin-2-yl)acetamide;
(12) N-{[4-(5,9-diethoxy-6-oxo-6,8-dihydro-7H-pyrrolo[3,4-g]quinolin-7-yl)-3-methylbenzyl]sulfonyl}-2-pyridin-2-ylpropanamide;
(13) N-({3-methyl-4-[6-oxo-5,9-bis(2,2,2-trifluoroethoxy)-6,8-dihydro-7H-pyrrolo[3,4-g]quinolin-7-yl]benzyl}sulfonyl)-2-pyridin-2-ylpropanamide;
(14) N-{[4-(5,9-diethoxy-6-oxo-6,8-dihydro-7H-pyrrolo[3,4-g]quinolin-7-yl)-3-methylbenzyl]sulfonyl}-2-(2-ethoxyphenyl)acetamide;
(15) N-{[4-(5,9-diethoxy-6-oxo-6,8-dihydro-7H-pyrrolo[3,4-g]quinolin-7-yl)-3-methylbenzyl]sulfonyl}-2,2-difluoro-2-phenylacetamide;
(16) N-{[4-(5,9-diisopropoxy-6-oxo-6,8-dihydro-7H-pyrrolo[3,4-g]quinolin-7-yl)-3-methylbenzyl]sulfonyl}-1-(2-methoxyphenyl)cyclopropanecarboxamide;
(17) N-{[4-(5,9-diethoxy-6-oxo-6,8-dihydro-7H-pyrrolo[3,4-g]quinolin-7-yl)-3-methylbenzyl]sulfonyl}-2-(2,6-dimethoxyphenyl)acetamide;
(18) 1-(2-methoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropanecarboxamide;
(19) N-{[4-(5,9-diethoxy-6-oxo-6,8-dihydro-7H-pyrrolo[3,4-g]quinolin-7-yl)-3-methylbenzyl]sulfonyl}-2-[2-(difluoromethoxy)phenyl]acetamide;
(20) N-{[4-(5,9-diethoxy-6-oxo-6,8-dihydro-7H-pyrrolo[3,4-g]quinolin-7-yl)-3-methylbenzyl]sulfonyl}-2-(2-methoxyphenyl)-N-methylacetamide;
(21) N-{[4-(5,9-diethoxy-6-oxo-6,8-dihydro-7H-pyrrolo[3,4-g]quinolin-7-yl)-3-methylbenzyl]sulfonyl}bicyclo[4.2.0]octa-1,3,5-triene-7-carboxamide;

(22) N-{[4-(5,9-dimethoxy-6-oxo-6,8-dihydro-7H-pyrrolo[3,4-g]quinolin-7-yl)-3-methylbenzyl]sulfonyl}-1-(2-methoxyphenyl)cyclopropanecarboxamide;

(23) 2-(2-methoxyphenyl)-N-methyl-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide;

(24) 1-(2,6-dichlorophenyl)-N-{[4-(5,9-diethoxy-6-oxo-6,8-dihydro-7H-pyrrolo[3,4-g]quinolin-7-yl)-3-methylbenzyl]sulfonyl}cyclopropanecarboxamide;

(25) N-{[4-(5,9-diethoxy-6-oxo-6,8-dihydro-7H-pyrrolo[3,4-g]quinolin-7-yl)-3-methylbenzyl]sulfonyl}-1-(2,6-dimethoxyphenyl)cyclopropanecarboxamide;

(26) 1-(2,6-dichlorophenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropanecarboxamide;

(27) N-{[3-bromo-4-(5,9-diethoxy-6-oxo-6,8-dihydro-7H-pyrrolo[3,4-g]quinolin-7-yl)benzyl]sulfonyl}-1-(2-methoxyphenyl)cyclopropanecarboxamide;

(28) 1-(2,6-dimethoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropanecarboxamide;

(29) N-({3-chloro-4-6-oxo-5,9-bis(2,2,2-trifluoroethoxy)-6,8-dihydro-7H-pyrrolo[3,4-g]quinolin-7-yl]benzyl}sulfonyl)-1-(2,6-dimethoxyphenyl)cyclopropanecarboxamide;

(30) N-({3-chloro-4-[6-oxo-5,9-bis(2,2,2-trifluoroethoxy)-6,8-dihydro-7H-pyrrolo[3,4-g]quinolin-7-yl]benzyl}sulfonyl)-1-(2-methoxyphenyl)cyclopropanecarboxamide;

(31) 1-(2-chloro-6-fluorophenyl)-N-{[4-(5,9-diethoxy-6-oxo-6,8-dihydro-7H-pyrrolo[3,4-g]quinolin-7-yl)-3-methylbenzyl]sulfonyl}cyclopropanecarboxamide;

(32) 1-(3-bromo-2,6-dimethoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropanecarboxamide;

(33) N-({4-[3-bromo-6-oxo-5,9-bis(2,2,2-trifluoroethoxy)-6,8-dihydro-7H-pyrrolo[3,4-g]quinolin-7-yl]-3-methylbenzyl}sulfonyl)-1-(2,6-dimethoxyphenyl)cyclopropanecarboxamide;

(34) 1-(2,6-diethylphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropanecarboxamide;

(35) 2-(2,6-difluorophenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide;

(36) 2-(2-bromophenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide;

(37) N-({3-methyl-4-[6-oxo-5,9-bis(2,2,2-trifluoroethoxy)-6,8-dihydro-7H-pyrrolo[3,4-g]quinolin-7-yl]benzyl}sulfonyl)-2-(2-methylphenyl)acetamide;

(38) 2-(5-bromo-2-methoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide;

(39) 2-(2,5-dimethoxyphenyl)-N-({3-methyl-4-[6-oxo-5,9-bis(2,2,2-trifluoroethoxy)-6,8-dihydro-7H-pyrrolo[3,4-g]quinolin-7-]benzyl}sulfonyl)acetamide;

(40) 1-(2,6-dimethylphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropanecarboxamide;

(41) 2-(2,3-dimethoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide;

(42) 2-(2,6-dimethoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)-2-oxoacetamide;

(43) 1-(3-hydroxy-2,6-dimethoxyphenyl)-N-({3-methyl-4-[6-oxo-5,9-bis(2,2,2-trifluoroethoxy)-6,8-dihydro-7H-pyrrolo[4-g]quinolin-7-yl]benzyl}sulfonyl)cyclopropanecarboxamide;

(44) 1-(5-bromo-2-methoxyphenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)cyclopropanecarboxamide;

(45) 2-(2,6-dimethoxyphenyl)-2-methoxy-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide; and

(46) 2-(2,3-dichlorophenyl)-N-({3-methyl-4-[6-oxo-5,9-bis(2,2,2-trifluoroethoxy)-6,8-dihydro-7H-pyrrolo[3,4-g]quinolin-7-yl]benzyl}sulfonyl)acetamide;

or a pharmaceutically acceptable salt of any of the aforementioned.

16. The compound according to claim 1 having the formula:

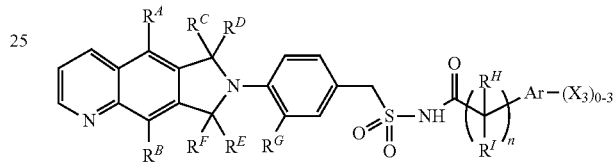

or a pharmaceutically acceptable salt thereof, wherein:

n is 0 or 1;

Ar is selected from the group consisting of: $C_{3-6}$cycloalkyl, aryl, heteroaryl and heterocyclyl, or a fused analog of $C_{3-6}$cycloalkyl, aryl, heteroaryl and heterocyclyl;

$R^A$ and $R^B$ are independently selected from the group consisting of $C_{1-4}$alkoxy, $C_{1-4}$fluoroalkoxy, $C_{3-6}$cycloalkoxy and $C_{3-6}$cycloalkylmethoxy;

$R^C$ and $R^D$ are hydrogen and $R^E$ and $R^F$ are joined together to form carbonyl;

$R^G$ is selected from the group consisting of: F, Cl, Br, I, methyl, ethyl, methoxy, $CF_3$, $CF_3O$— and CN;

$R^H$ and $R^I$ are independently hydrogen or methyl; or $R^H$ and $R^I$ may be joined together to form a $C_{3-6}$cycloalkyl ring; and each $X_2$ and $X_3$ is independently selected from the group consisting of: F, Cl, Br, I, methyl, ethyl, methoxy, $CF_3$, $CF_3O$— and OH.

17. A compound having the formula:

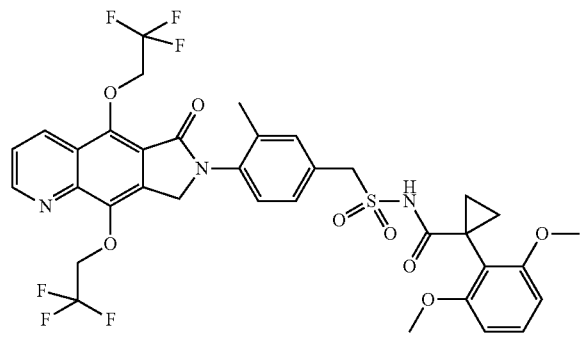

or a pharmaceutically acceptable salt thereof.

* * * * *